(12) United States Patent
Lampidis et al.

(10) Patent No.: US 8,242,167 B2
(45) Date of Patent: Aug. 14, 2012

(54) MANNOSE DERIVATIVES FOR KILLING TUMOR CELLS

(75) Inventors: Theodore J. Lampidis, Miami, FL (US); Metin Kurtoglu, Miami, FL (US); Johnathan C. Maher, Miami, FL (US)

(73) Assignee: University of Miami, Miami, FL (US)

( * ) Notice: Subject to any disclaimer, the term of this patent is extended or adjusted under 35 U.S.C. 154(b) by 18 days.

(21) Appl. No.: 12/280,541

(22) PCT Filed: Feb. 26, 2007

(86) PCT No.: PCT/US2007/004845
§ 371 (c)(1),
(2), (4) Date: Dec. 8, 2008

(87) PCT Pub. No.: WO2007/100728
PCT Pub. Date: Sep. 7, 2007

(65) Prior Publication Data
US 2009/0221698 A1 Sep. 3, 2009

Related U.S. Application Data

(60) Provisional application No. 60/776,793, filed on Feb. 24, 2006.

(51) Int. Cl.
*A61K 31/35* (2006.01)
(52) U.S. Cl. ...................................................... 514/460
(58) Field of Classification Search ........................ None
See application file for complete search history.

(56) References Cited

U.S. PATENT DOCUMENTS

| | | | | |
|---|---|---|---|---|
| 6,667,030 | B1 * | 12/2003 | Schneider | 424/76.1 |
| 6,670,330 | B1 * | 12/2003 | Lampidis et al. | 514/23 |
| 6,979,675 | B2 | 12/2005 | Tidmarsh | |
| 7,160,865 | B2 * | 1/2007 | Lampidis et al. | 514/23 |
| 7,338,940 | B2 * | 3/2008 | Lampidis et al. | 514/23 |
| 2003/0181393 | A1 * | 9/2003 | Lampidis et al. | 514/23 |
| 2004/0043250 | A1 | 3/2004 | Ise | |
| 2004/0167079 | A1 * | 8/2004 | Tidmarsh | 514/23 |
| 2005/0043250 | A1 * | 2/2005 | Lampidis et al. | 514/23 |
| 2005/0245462 | A1 | 11/2005 | Tidmarsh | |
| 2006/0025351 | A1 * | 2/2006 | Lampidis et al. | 514/23 |

OTHER PUBLICATIONS

Aft et al .(British Journal of Cancer 2002; 87: 805-812).*
Aft et al. (British Journal of Cancer 2002; 87: 805-812).*
Maher et al (Cancer Chemother Pharmacol, 2004, 53:116-122, IDS).*
Aft et al (British Journal of Cancer, 2002, 87:805-812).*
Lin et al (Cancer Research, 2003, 63:3413-3417).*
Kurtoglu et al (Proc Amer Assoc Cancer Res., Apr. 2005, 46:abstract 2375, IDS).*
Maher et al (Pancreas, Mar. 2005, 30:e34-e39).*
Kurtoglu Metin et al: "2-deoxy-D-glucose kills select tumor cell types under normoxia: reversal by mannose indicates interference with glycosylation." Proceedings of the American Association for Cancer Research Annual Meeting, vol. 46, Apr. 2005, p. 557, XP001569606 & 96th Annual Meeting of the American-Association-for-Cancer-Research; Anaheim, CA, USA; Apr. 16-20, 2005.
Maher Johnathan C et al: "Greater cell cycle inhibition and cytotoxicity induced by 2-deoxy-D-glucose in tumor cells treated under hypoxic vs aerobic conditions." Cancer Chemotherapy and Pharmacology, vol. 53, No. 2, Feb. 2004, pp. 116-122.
Maschek G et al: "2-deoxy-D-glucose increases the efficacy of adriamycin and paclitaxel in human osteosarcoma and non-small cell lung cancers in vivo" Cancer Research, American Association For Cancer Research, Baltimore, MD., US, vol. 64, No. 1, Jan. 1, 2004, pp. 31-34.
Beckner, et al. "Glycotic glioma cells with active glycogen synthase are sensitive to PTEN and inhibitors of P13K and gluconeogenesis." Laboratory Investigation. 85, 1457-1470 (2005).
Bren, et al. "Metabolomics: Working Toward Personalized Medicine." FDA Consum. 39(6), 28-33 (Nov.-Dec. 2005).
International Search Report, for PCT/US07/04845, dated Aug. 12, 2008.
Lampidis, et al. "Efficacy of 2-halogen substituted D-glucose analogs in blocking glycolysis and killing 'hypoxic tumor cells.'" Cancer Chemother. Pharmacol. 58: 725-734 (2006).
Meadows M. Genomics and Personalized Medicine, FDA Consum. 39(6), 12-7 (Nov.-Dec. 2005).
Sadee, et al. "Pharmacogenetics/Genomics and Personalized Medicine." Hum. Mol. Genet. 14 Spec. No. 2: R207-214 (2005).
Schnackenberg, et al. "Monitoring the Health to Disease Consortium with Global Metabolic Profiling and Systems Biology." Pharmacogenomics. 7(7), 1077-1086 (Oct. 2006).
van der Greef, et al. "Metabolomics-Based Biology and Personalized Medicine." Pharmacogenomics. 7(7), 1087-1094 (Oct. 2006).
Warner et al. "Diagnostics + Therapy = Theranostics." The Scientist, 18(16), 38 (2004).

* cited by examiner

*Primary Examiner* — Laura B Goddard

(74) *Attorney, Agent, or Firm* — Novak Druce + Quigg LLP

(57) ABSTRACT

A method for treating cancer by killing selected tumor cells such as human breast, non-small cell lung cancer cells, pancreatic cancer cells, osteosarcoma cancer cells, and glioblastoma cells, includes administering to a patient in need of treatment, an effective amount of at least one mannose analog such as 2-DG or 2-FM or 2-CM. The killing is believed to be due to an interference with glycosylation. A theranostic method includes determining whether a patient. cancer tumor sample comprises cells sensitive to killing to at least one mannose analog due to an interference with glycosylation.

17 Claims, 7 Drawing Sheets

MANNOSE DERIVATIVES FOR KILLING TUMOR CELLS

RELATED APPLICATIONS

This application claims the benefit under 35 U.S.C. §119(e) of U.S. Provisional Application No. 60/776,793, filed on Feb. 24, 2006, which is hereby incorporated by reference herein in its entirety.

GOVERNMENT SUPPORT

Work described herein may have been supported in part by NIH Grant number 2RO1 CA037109. The U.S. Government may have certain rights in the invention.

BACKGROUND OF THE INVENTION

The present invention relates generally to the field of medicine, particularly to the treatment of cancer, and more particularly, to new and useful methods for treating certain types of cancer sensitive to particular glycoside compounds.

Although molecular biology has provided new possibilities for selectively targeting and killing tumor cells without harming normal cells, current clinical chemotherapy still relies primarily on agents that kill rapidly-dividing cells regardless of whether those cells are normal or malignant.

Rapidly-dividing normal cells include cells of the bone marrow and intestine. As these are among the most rapidly-dividing normal tissues, the acute dose-limiting toxicities of most anti-cancer agents often involve bone marrow depression and gastro-intestinal side effects. Fortunately, most normal organs and tissues in humans are comprised of cells that are either slow-growing or non-proliferating, which accounts for their relative resistance to chemotherapy. Thus, the window of selectivity of the standard anti-cancer agents used today is not between normal and tumor but between rapid vs slow replicating cells. Viewing the window of selectivity in this manner highlights that the slow-growing tumor cell population found in most if not all solid tumors presents one of the most difficult obstacles to overcome in the successful treatment of the majority of human cancers with chemotherapy or radiation.

The use of glycolytic inhibitors as new chemotherapeutics to overcome this obstacle is disclosed in U.S. Pat. No. 6,670,330, issued Dec. 30, 2003, entitled "Cancer chemotherapy with 2-deoxy-D-glucose" and incorporated herein by reference. This patent discloses that the hypoxic micro-environment of the slow-growing tumor cell population within solid tumors distinguishes these cells metabolically from the majority of the normal cells in the body that are also slow-growing but under normal oxygen tension. Consequently, because hypoxia forces cells to rely primarily or exclusively on the anaerobic metabolism of glucose for survival, hypoxic tumor cells can be selectively targeted with inhibitors of glycolysis, such as 2-deoxy-D-glucose (2-DG). This patent also discloses that glycolytic inhibitors such as 2-DG can be used in combination with standard chemotherapeutic agents that target rapidly-dividing cells so that all cells in a tumor can be killed during cancer treatment. U.S. Pat. No. 6,979,675, issued 27 Dec. 2005 and incorporated herein by reference, also focuses on the use of 2-DG in the treatment of cancer and describes various combination therapies for that purpose. Clinical trials evaluating the efficacy of 2-DG in combination with docetaxel in the treatment of patients suffering a variety of solid tumors are ongoing.

Cancer therapies employing the glycolytic inhibitor 2-DG benefit from two windows of selectivity that result when a cell switches from aerobic to anaerobic metabolism, as occurs in cancer cells that become, due to tumor growth, removed from the blood (and hence oxygen) supply.

The first is that tumor cells under hypoxia up-regulate expression of both glucose transporters and glycolytic enzymes, which favors increased uptake of the glucose analog 2-DG in these cells as compared to normal cells in an aerobic environment. The second is that blocking glycolysis in normal cells in an aerobic environment does not kill those cells, because they can survive by using oxygen to burn fat and protein in their mitochondria to produce energy (via energy-storing molecules such as ATP). In contrast, when glycolysis is blocked in tumor (or normal) cells in a hypoxic environment, those cells will die, because without oxygen, those cells are unable to produce energy via mitochondrial oxidation of fat and protein.

These two windows of selectivity provide the rationale upon which better use of glycolytic inhibitors in raising the efficacy of current chemotherapy can be developed, by targeting the slow-growing hypoxic cell population found in most, if not all, solid tumors.

2-DG is known to compete with glucose for transport into the cell as well as for the binding site on hexokinase, where glucose is phosphorylated at carbon 6 in the first step of glycolysis. For 2-DG, however, the product of this step is 2-DG-6P, which accumulates intracellularly and competitively inhibits the next step in the glycolytic pathway, catalyzed by phosphoglucose isomerase, which normally converts glucose-6-phosphate to fructose-6-phosphate. Inhibition of this second step of glycolysis can prevent the cell from creating energy by anaerobic glycolysis.

Therefore, the greater the amount of 2-DG-6P produced by the hexokinase reaction, the greater the effect on glycolysis. Because 2-DG is orally available and relatively non-toxic, it is an ideal glycolytic inhibitor. However, molecular modeling of human hexokinase I interactions and experimental testing with a series of 2-halogen-substituted D-glucose derivatives has revealed that certain 2-halogen substituted glucose analogs may be as, if not more, effective than 2-DG in inhibiting glycolysis in cancer cells. These observations are consistent with the use of 2-FG (2-deoxy-2-fluoro-D-glucose) as a highly effective agent for visualizing tumors by PET scan.

While the promise of glycolytic inhibitors in the treatment of cancer is great, not all cancer cells exist in a hypoxic environment, and combination therapies are typically more difficult for both the patient and physician than therapies requiring only a single agent. There remains a need for cancer therapies that require the administration of only a single agent, particularly agents that can be orally administered in high doses, such as 2-DG and its 2-halo analogs.

Current cancer therapies are focused on the patient's illness rather than targeted to individual patients. However, interindividual differences in drug disposition or pharmokinetics have led to heterogeneity in patient responses to traditional cancer chemotherapy. There remains a need for cancer therapies that are more accurate, efficacious, and safe for individual patients. The invention meets this and other important needs.

SUMMARY OF THE INVENTION

It is an object of the present invention to provide a method for killing certain types of tumor cells by administering 2-DG (2-deoxy-D-glucose), 2-FM (2-deoxy-2-fluoro-mannose), 2-deoxy-2-chloro-mannose (2-CM), or a combination of two or more of these agents. In one embodiment, the 2-DG or 2-FM or 2-CM is administered to a patient suffering from a cancer harboring the selected tumor cell types with or without additional anti-tumor treatments.

Another object of the invention is to provide a method for treating cancer by killing certain types of tumor cells, such as human breast, non-small cell lung cancer cells, pancreatic cancer cells, osteosarcoma cancer cells, and glioblastoma cancer cells which comprises administering to a patient in need of treatment an effective amount of 2-DG or 2-FM or 2-CM, or a combination of two or more of these agents. In some embodiments, the tumor cells are 2SKBR3, 1420, HELA, S-1, S-2, TG98, or RT8228 cells.

Another object of the invention is to provide a method for killing a cancer cell that is not in a hypoxic environment by the administration of an agent that interferes with glycosylation. In one embodiment, the agent is 2-DG. In another embodiment, the agent is 2-FM. In another embodiment, the agent is 2-CM. In another embodiment, a combination of two or more of these agents is employed in the method.

Another object of the invention is to provide a method for killing normoxic tumor cells by the administration of at least one mannose analog, wherein the normoxic tumor cells are sensitive to at least one mannose analog under normoxia. In one embodiment, the mannose analog is 2-DG. In another embodiment, the mannose analog is 2-FM. In another embodiment, the mannose analog is 2-CM. In another embodiment, a combination of two or more of these mannose analogs is employed in the method.

Another object of the invention is to provide theranostic methods. In one embodiment, the theranostic method comprises determining whether a patient cancer tumor sample comprises cells sensitive to killing due to an interference with glycosylation. In another embodiment, the theranostic method comprises determining whether a patient cancer tumor sample comprises cells sensitive to at least one mannose analog.

In one aspect, the theranostic method can comprise the steps of: isolating cells from a patient cancer tumor, testing the cells ex vivo for sensitivity to at least one mannose analog under normoxic conditions, and testing the cells ex vivo for sensitivity to the at least one mannose analog under hypoxic conditions, wherein the detection of sensitivity to the at least one mannose analog under normoxic conditions and lack of sensitivity to the at least one mannose analog under hypoxic conditions results in the determination that the patient cancer tumor sample comprises cells sensitive to killing due to an interference with glycosylation under normoxia or the determination that the patient cancer tumor sample comprises cells sensitive to at least one mannose analog.

In another aspect, the theranostic method can comprise the steps of: isolating cells from a patient tumor and comparing the molecular signature of cells from a patient sample with the molecular signatures of closely related mannose analog sensitive and resistant cell lines, wherein a substantial similarity in the molecular signature of the cells from the patient sample to the molecular signature of a mannose analog sensitive cell line results in the determination that the patient cancer tumor sample comprises cells sensitive to killing due to an interference with glycosylation under normoxia or the determination that the patient cancer tumor sample comprises cells sensitive to at least one mannose analog.

In some aspects, the theranostic methods further comprise killing the sensitive tumor cells with an effective amount of at least one mannose analog.

The various features of novelty which characterize the invention are pointed out with particularity in the claims annexed to and forming a part of this disclosure. For a better understanding of the invention, its advantages, and specific objects attained by its uses, reference is made to the accompanying drawings and descriptive matter in which preferred embodiments of the invention are illustrated.

DETAILED DESCRIPTION OF THE INVENTION

Figure 1:
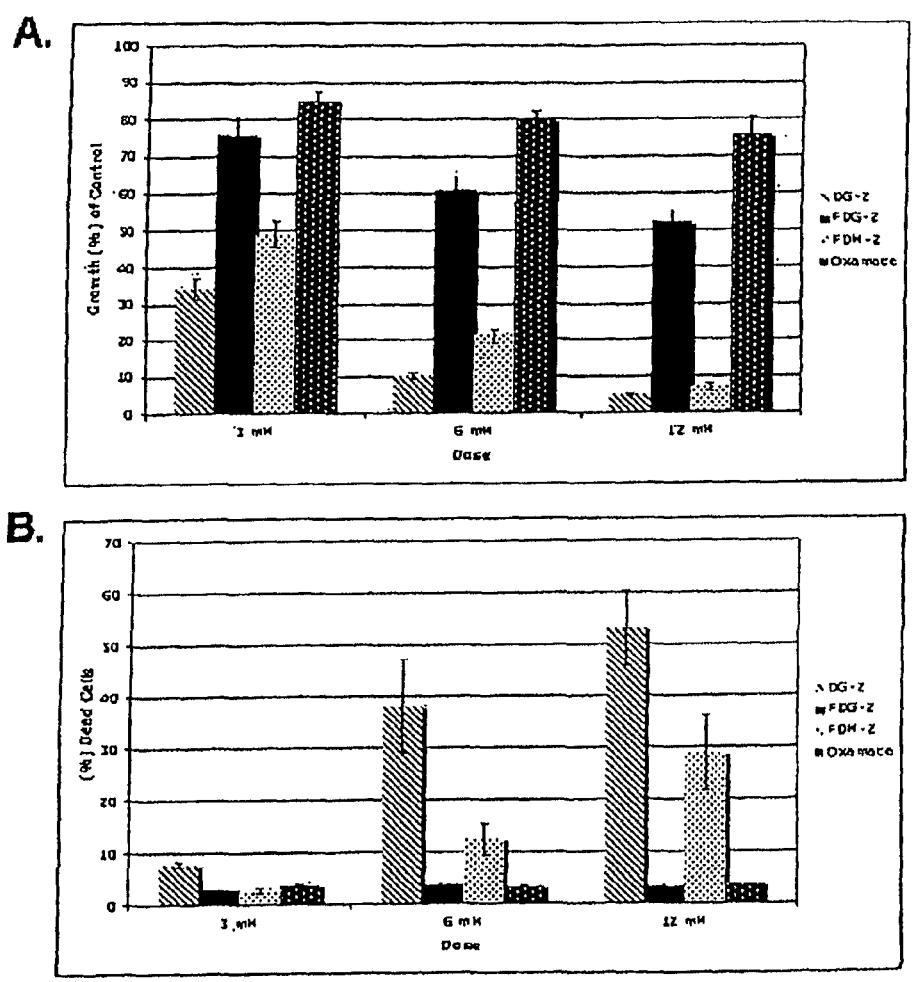
FIG. 1 shows growth inhibitory (A) or cytotoxic (B) assays in SKBR3 cells following treatment with either 2-DG, 2-FDG, 2-FDM or oxamate for 24 hrs. Each value is the average±SD of triplicate samples.

For the purposes of promoting an understanding of the principles of the invention, reference will now be made to specific embodiment and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates.

All terms as used herein are defined according to the ordinary meanings they have acquired in the art. Such definitions can be found in any technical dictionary or reference known to the skilled artisan, such as the *McGraw-Hill Dictionary of Scientific and Technical Terms* (McGraw-Hill, Inc.), *Molecular Cloning: A Laboratory Manual* (Cold Springs Harbor, N.Y.), *Remington's Pharmaceutical Sciences* (Mack Publishing, PA), and *Stedman's Medical Dictionary* (Williams and Wilkins, MD). These references, along with those references and patents cited herein are hereby incorporated by reference in their entirety.

2-DG is currently being administered in a clinical trial to evaluate the extent to which the addition of a glycolytic inhibitor, which kills slow-growing hypoxic tumor cells, the most resistant cell population found in solid tumors, can increase treatment efficacy of standard chemotherapy targeting rapidly-dividing normoxic cells. The invention arose in part from the discovery that, even in the presence of oxygen, certain tumor cell lines are killed when treated with 2-DG or 2-FM but not when 2-deoxy-2-fluoro-D-glucose (2-FG) is administered. Because 2-FG and 2-DG both inhibit glycolysis, a mechanism other than blockage of glycolysis was presumed responsible for this effect.

Studies conducted in the 1970's led to reports that 2-DG and 2-FM interfere with N-linked glycosylation of viral coat glycoproteins, which interference can be reversed by the addition of mannose. Because the difference between mannose and glucose lies only in the orientation of the hydrogen at the 2-carbon position, and because 2-DG has two hydrogens at the 2-position (instead of a hydrogen and a hydroxyl group, as is the case for both mannose and glucose, 2-DG can be viewed either as a mannose or a glucose analog. Accordingly, 2-DG can be predicted to be able to act on both glycolysis and glycosylation.

Thus, the invention provides methods to kill selected tumor cells regardless of the whether the cells are in a hypoxic or normoxic environment, using mannose derivatives (including 2-DG) alone, or in combination with other anti-tumor treatments, including but not limited to cytotoxic agents that target normoxic cells, anti-angiogenic agents, radiation therapy, and surgery. The invention also provides a basis for the clinical use of a mannose analog such as 2-DG, 2-CM, and 2-FM as cytotoxic agents that can target both normoxic (via interference with glycosylation) and all hypoxic (via blockage of glycolysis) cancer cell populations in certain tumor types.

As used herein, the term "normoxia" refers to a state in which the partial pressure of oxygen is equal to that of air pressure at sea level, and the term "hypoxia" refers to decreased levels of oxygen below normal levels. It is further contemplated by the invention that the determination of normoxic and hypoxic conditions may be dependent on the characteristics and environment of the individual patient and/or of the individual tumor mass.

Mannose Analogs are Toxic to Select Tumor Cell Types Growing Under Normoxia Due to Interference with Glycosylation The examples below provide data that verify the effectiveness of the invention and confirms that 2-DG, 2-CM, and 2-FM, but not 2-FG, are toxic to select tumor cell types growing under normoxia. The experiments described in the examples were designed to determine whether interference with glycosylation as opposed to inhibition of glycolysis is the mechanism responsible for the normoxic effect. While not wishing to be bound by theory, the results support the notion that these compounds can inhibit glycosylation and thereby kill certain cancer cell types independently of whether those cells are in a hypoxic environment.

The invention arose in part from the surprising discovery that, in the presence of oxygen (normoxic conditions), 2-DG is toxic to a subset of tumor cell lines. This result was surprising because previous research demonstrated that tumor and normal cells are growth inhibited but not killed when treated with 2-DG under normoxia. This prior observation of growth inhibition was believed to be due to the accumulation of 2-DG to levels high enough to block glycolysis in cells under normoxia so that growth was reduced because of reduction in the levels of the intermediates of the glycolytic pathway, which are used for various anabolic processes involved with cell proliferation. The cells do not die, however, because if mitochondrial function is normal, then aerobically treated cells can survive blockage of glycolysis by 2-DG. One possible explanation for how a cell could be sensitive to 2-DG under normoxic conditions is, therefore, that the cell has defective mitochondria. In this regard, it is known that tumor cells utilize glucose through anaerobic glycolysis for the production of energy (ATP) instead of oxidative phosphorylation due to defective mitochondrial respiration. However, further experiments have demonstrated that other inhibitors of glycolysis, such as oxamate and 2-FG, are not toxic to these cells, so a defect in mitochondrial respiration is unlikely to account for their sensitivity to 2-DG. It was therefore hypothesized that a mechanism other than blockage of glycolysis is responsible for 2-DG toxicity in these select cell lines under normoxic conditions.

Accordingly, other hypotheses were developed to explain the mechanism of this normoxic cytotoxicity. One potential mechanism was interference with glycosylation. Support for this potential mechanism could be identified in a series of papers from the late 1970's in which it was reported that, in certain viruses, N-linked glycoprotein synthesis was inhibited by a number of sugar analogs, including 2-DG.

Figure 7:
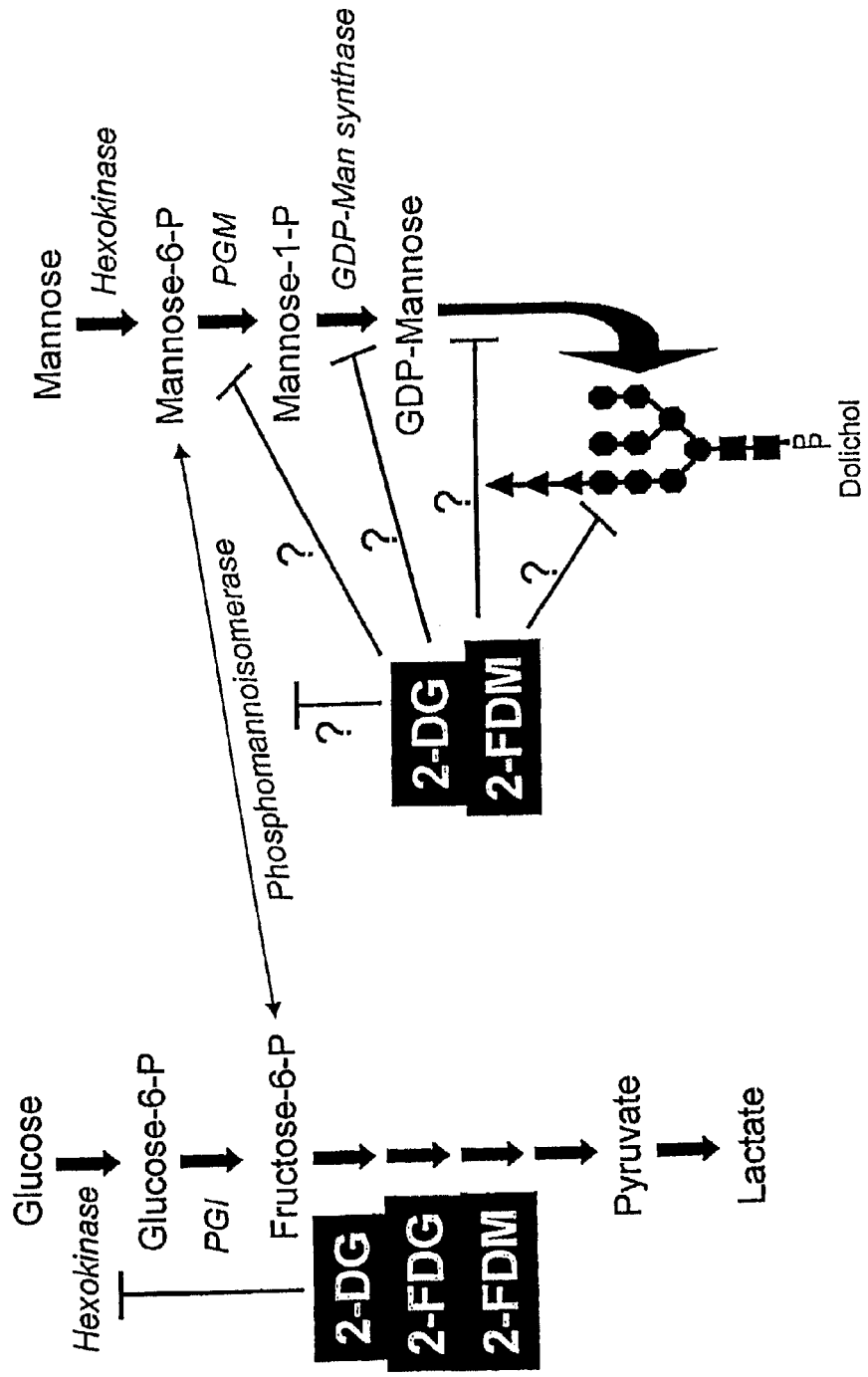
FIG. 7 shows glycolysis and N-linked glycosylation pathways to illustrate that 2-DG, 2-FDM and 2-FDG can inhibit phosphoglucoisomerase resulting in blockage of glycolysis and ensuing cell death in hypoxic tumor cells. However, in certain tumor cell types under aerobic conditions, 2-DG and 2-FDM can interfere with lipid-linked assembly of oligosaccharides leading to induction of unfolded protein response and toxicity, because their structures resemble mannose as well as glucose. (triangle=glucose, hexagon=mannose and square=N-acetyl-glucosamine)

Glucose is metabolized through three major pathways: glycolysis, pentose phosphate shunt and glycosylation. FIG. 7 is a scheme diagram of the glycolysis and glycosylation metabolic pathways. After glucose enters the cytoplasm, hexokinase phosphorylates carbon 6 of glucose, resulting in synthesis of glucose-6-phosphate (G6P). If G6P is converted to fructose-6-phosphate by phosphoglucose isomerase (PGI), it can continue on the glycolysis pathway and produce ATP and pyruvate. Alternatively, G6P can also be used for synthesis of various sugar moieties, including mannose, which is required for assembly of lipid-linked oligosaccharides, the synthesis of which is performed in the ER. 2DG has been shown to interfere with two of the three metabolic pathways: it can block glycolysis by inhibiting PGI or it can disrupt the assembly of N-linked oligosaccharide precursor by interfering with the transfer of guanosine diphosphate (GDP) dolichol phosphate linked mannoses onto the N-acetylglucosamine residues and can deplete dolichol-P, which is required to transfer mannose from the cytoplasm to the lumen of the ER.

Experimental observation showed that 2-DG and 2-FM inhibit the assembly of lipid-linked oligosaccharides resulting in the disruption of high mannose type protein glycosylation. Structurally, 2-DG resembles mannose as well as glucose, and in the process of N-linked glycosylation, 2-DG was shown to mimic mannose in its stepwise addition to the lipid linked oligosaccharide chain. As noted above, because 2-DG has hydrogens at both positions of carbon 2, 2-DG can be considered both a glucose and a mannose analog. In contrast, the presence of a fluoride at this position in fluoro analogs creates a new enantiomeric center, and so the fluoro derivatives can only be considered analogs of either glucose or mannose; in depicting these analogs, the fluoride moiety is drawn "up" or above the plane of the carbohydrate ring for mannose analogs, and down for the glucose analogs.

For mannose to be added to a lipid-linked oligosaccharide chain, it must first be activated by being transferred to guanosine diphosphate (GDP) or dolichol phosphate. 2-DG undergoes conversion to 2-DG-GDP, which competes with mannose-GDP for the addition of mannose onto N-acetyl-glucosamine residues during the assembly of lipid-linked oligosaccharides. Thus, the aberrant oligo-saccharides produced as a result of 2-DG treatment resulted in decreased synthesis of the viral glycoproteins in the experiments reported in the scientific literature. In these experiments, the inhibitory effect of 2-DG was reversed with addition of exogenous mannose but not when glucose was added, further confirming that 2-DG was acting as a mannose analog. These investigators also showed that another mannose analog, 2-fluoro-mannose (2-FM), had similar effects as 2-DG that were also reversed by mannose, indicating that the mannose configuration of these analogs was important for their interference with glycosylation.

In addition, genetic studies have shown that disruption of glycosylation can have profound biological effects. The enzyme phosphomannose isomerase (PMI) is absent in patients suffering from Carbohydrate-Deficient Glycoprotein Syndrome Type 1b. The absence of this enzyme results in hypoglycosylation of serum glyco-proteins, leading to thrombosis and gastrointestinal disorders characterized by protein-losing enteropathy. When exogenous mannose is added to the diets of these patients, their symptoms disappeared, their serum glycoproteins returned to normal, and they recovered from the disease. This observation is consistent with a mechanism of action for the compounds useful in the present invention, as experimental data show that exogenous mannose can rescue the selected tumor cells that are killed when treated with 2-DG in the presence of normal oxygen levels. It is possible that these particular tumor cells are either down-regulating PMI or have a defect in this enzyme. On the other hand, enzymes that produce mannose intermediates necessary for N-linked glycosylation may be up-regulated in these cells, resulting in a higher 2-DG-GDP to mannose-GDP ratio and thereby causing this unusual sensitivity to 2-DG under normal oxygen conditions.

Regardless of mechanism, the present invention provides methods for treating cancer by administering 2-DG and other mannose analogs as single agents for treating select tumor types that are sensitive to these agents even under normoxic conditions. The invention has been demonstrated to be effective against a number of tumor cells lines, including human breast (SKBR3), non small cell lung (NSCLC), pancreatic and osteosarcoma cancer cell lines, all of which undergo significant cell death when treated with relatively low doses of 2-DG.

Figure 3:
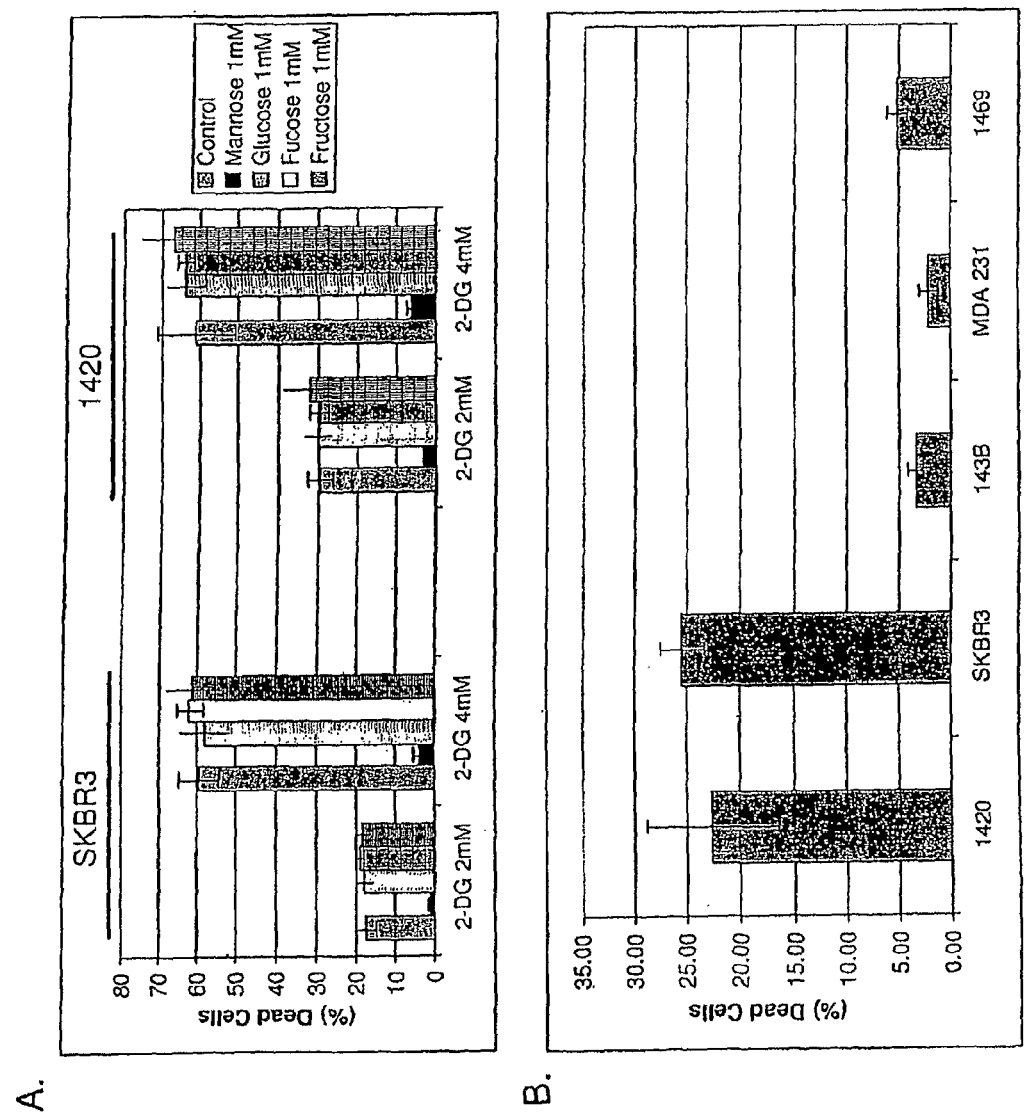
FIG. 3 shows (A) 2-DG induced toxicity can be reversed by low dose of mannose. 1420 and SKBR3 cells were treated with increasing concentrations of 2-DG in conjunction with 1 mM of various sugars followed by analysis of cytotoxicity with trypan blue exclusion assays. Each value is the average+ SD of triplicate samples. It was noted that only mannose could reverse the 2-DG toxicity while other sugars, i.e. glucose, fucose and fructose had no effect. (B) 2-FDM caused toxicity in 2-DG sensitive but not 2-DG resistant cell types. Cytotoxicity was assayed following treatment with 4 mM of 2-FDM to further support the hypothesis that the manno-configuration of the sugar analogs is central for their toxic effects.

FIG. 3 (B) is a chart showing the response of SKBR3 cells treated for 72 hrs with 2-DG, 2-FM and other agents under normal oxygen conditions at the doses indicated. Cytotoxicity was measured by trypan blue exclusion. The results show that 2-DG and the mannose analog 2-FM are toxic, while 2-FG, a glucose analog is not. Moreover, oxamate, an analog of pyruvate that blocks glycolysis at the lactic dehydrogenase level, is also not toxic to these cells growing under normoxic conditions. In contrast, the mannose analog, 2-FM also proved to be toxic in these cells, again indicating that a mannose backbone was important for compounds having this activity.

The inhibitory effect of 2-DG was reversed with addition of exogenous mannose but not when glucose was added, further confirming that 2-DG is acting as a mannose analog. Other testing showed that 2-DG is also toxic to a NSCLC growing under normoxic conditions and that addition of 1 mM mannose reverses this toxicity.

This data further supports that 2-DG and 2-FM are toxic to select tumor cells growing under normoxic conditions due to interference with glycosylation. Additional evidence that these mannose analogs are working through this mechanism and not through blockage of glycolysis is that the unfolded protein response proteins, GRP 78 and 94, indicative of misfolded and or mis-glycosylated proteins are up-regulated by 2-DG and 2-FM in a dose-dependent manner but not by 2-FG; this effect is likewise reversed by addition of mannose.

Thus, the mannose analogs 2-DG and 2-FM, but not the glucose analog 2-FG, are toxic to select tumor cell types growing under normoxia, and the addition of mannose reverses this toxicity. Because 2-FG inhibits glycolysis better than 2-DG, interference with glycosylation and not inhibition of glycolysis is the mechanism believed to be responsible for this effect. As mentioned above, it has been reported that 2-DG interferes with N-linked glycosylation of viral coat proteins and that exogenously added mannose reverses the effect. The toxic effects of 2-DG on SKBR3, NSCLC and two other human tumor cell lines under normoxia are therefore likely to be due to interference of glycosylation. If this mechanistic theory is correct, then addition of mannose should reverse the toxicity of 2DG in these cell lines. Indeed, 1 mM of mannose reverses the toxic effects of 6 mM of 2DG in one of the cell lines tested (NSCLC).

Because blood levels of mannose are known to range between 50 and 60 micro g/ml, dose-response experiments to determine the minimal mannose dose necessary to reverse 2-DG toxicity can be performed. For example, this can be achieved by experiments in which growth medium is supplemented with dialyzed fetal bovine serum (FBS), because FBS normally contains residual amounts of mannose. Moreover, to confirm that the addition of mannose and not other sugars is required to reverse 2-DG toxicity, sugars known to participate in glycoprotein synthesis, i.e. glucose, fucose, galactose, and the like, can be tested for the ability to reverse 2-DG toxicity. If any of these sugars is able to reverse toxicity similarly, then their activity can be compared to that of mannose in the experiments described below for reversing the effects of 2-DG in inducing UPR and its consequences, interference with oligosaccharide chain elongation, and binding of conconavalin A. Overall, these experiments allow one to assess in vitro the dose of 2-DG or 2-FM that can be used in vivo to yield anti-tumor activity in the presence of physiologic concentrations of mannose. The therapeutically effective dose of orally administered 2-DG, 2-FM, and 2-CM for use in the methods of the invention will, however, typically be in the range of 5-500 mg/kg of patient weight, such as 50-250 mg/kg. In one embodiment, the dose is about 100 mg/kg of patient weight.

Diagnostic and Theranostic Methods

The invention provides diagnostic and theranostic methods useful to determine whether a tumor or other cancer includes cells susceptible to the treatment methods of the invention. The term "theranostics" generally refers to therapy-specific diagnostics, which is the use of diagnostic testing to diagnose the disease, choose the correct treatment regime for that disease, and monitor the patient response to therapy. Theranostic tests can be used to predict and assess drug response in individual patients, and are designed to improve drug efficacy by selecting patients for treatments that are particularly likely to benefit from the treatments. Theranostic tests are also designed to improve drug safety by identifying patients that may suffer adverse side effects from the treatment.

Examples of targeted cancer therapies currently available include evaluation of breast cancer tumors for HER2 protein expression prior to treatment with Herceptin, testing of chronic myeloid leukemia for constitutive activity of the fusion protein BCR/ABL prior to treatment with Gleevac, and testing for activating mutations of the EGFR gene in lung cancers prior to treatment with Iressa. For general reviews of theranostics and targeted therapies, see Meadows M., Genomics and Personalized Medicine, FDA Consum. 2005 November-December; 39(6):12-7; Bren L., Metabolomics: Working Toward Personalized Medicine, FDA Consum. 2005 November-December; 39(6):28-33; Schnackenberg L. and Beger R., Monitoring the Health to Disease Continuum with Global Metabolic Profiling and Systems Biology, Pharmacogenomics 2006 October; 7(7): 1077-86; van der Greef J, Hankemeier T, and McBurney R., Metabolomics-Based Systems Biology and Personalized Medicine, Pharmacogenomics 2006 October; 7(7):1087-94; Warner S, Diagnostics+Therapy=Theranostics, The Scientist 2004, 18(16):38; Sadee W and Dai Z., Pharmacogenetics/Genomics and Personalized Medicine, Hum Mol Genet 2005, 14 Spec No. 2: R207-14, incorporated herein by reference.

In some embodiments, the invention provides theranostic methods for cancer. The methods can comprise determining whether a patient cancer tumor sample comprises cells sensitive to killing due to an interference with glycosylation. The methods can also comprise determining whether a patient cancer tumor sample comprises cells sensitive to killing by at least one mannose analog. In another aspect, the theranostic methods of the invention further comprise killing the sensitive tumor cells with an effective amount of at least one mannose analog.

In one embodiment, cells from a tumor are tested under normoxic conditions to determine if they are sensitive to killing due to an interference with glycosylation or if they are sensitive to at least one mannose analog. For example, cells may be isolated from a tumor and tested ex vivo to determine if the cells are sensitive to 2-DG, 2-CM, or 2-FM under normoxic conditions. In another embodiment, this testing is conducted; then, mannose is added to determine if it reverses the cytotoxic effects.

The invention further provides methods for determining whether any particular tumor type is sensitive to an interference with glycosylation and therefore susceptible to treatment with mannose analogs. The examples below illustrate methods for determining whether a cell is sensitive. In some embodiments, molecular signatures of closely related 2-DG sensitive and resistant cell pairs are compared to a test cell line. Such molecular signatures include differences in the level and/or activity of phosphomannose isomerase and other enzymes involved in glycosylation and enzymes involved in 2-DG accumulation. Using the methods of the invention, tumor cell types that are sensitive to 2DG, 2-FM, and 2-CM under normoxic conditions have been identified.

In one embodiment, the test for susceptibility to interference with glycosylation is performed using N-linked glycosylation as an indicator. 2-DG and 2-FM but not 2-FG disrupt the assembly of lipid linked oligosaccharide chains, (2) induce an unfolded protein response (UPR), which is an indicator of interference with normal glycoprotein synthesis, and (3) activate UPR-specific apoptotic signals in 2-DG sensitive but not resistant cells. Additionally, mannose reverses these effects. Accordingly, these same tests can be performed on a tumor or cancer cell of interest to determine if that cell is susceptible to treatment with the present method.

As noted above, the incorporation of mannose into a lipid-linked oligosaccharide chain occurs on the cytoplasmic surface of the ER in virus-infected cells, and this incorporation can be inhibited by GDP derivatives of 2-DG or 2-FM, i.e. GDP-2DG and GDP-2-FM. Normally, after the fifth mannose has been added, the lipid-linked oligosaccharide chain flips to face the lumen of the ER. To continue adding mannose to the growing chain, dolichol-phosphate (Dol-P) is used as a carrier to transport mannose from the cytoplasm to the matrix of ER. 2-DG-GDP competes with mannose-GDP for binding to dolichol and thereby further interferes with N-linked glycosylation. Moreover, dolichol-linked 2-DG also competes with the transfer of mannose onto the oligosaccharide chain in the ER. Accordingly, experiments can be performed to demonstrate the effects of 2-DG and 2-FM on the formation of lipid linked oligosaccharide precursors and the derivatives of mannose, i.e. mannose-6-phosphate, mannose-1-phosphate, GDP-mannose and Dol-P-mannose in both 2-DG sensitive and resistant cell lines. This in turn demonstrates the step or steps in oligosaccharide assembly that are inhibited by 2-DG and 2-FM. This in turn allows one to characterize other cell types as sensitive or resistant based on the oligosaccharides produced (and not produced) upon exposure to 2-DG, 2-FM, and/or 2-CM.

Previously established chromatographic methods can be used to collect and measure the amount of mannose derivatives and lipid-linked oligosaccharide precursors in SKBR3 and NSCLC cells. Briefly, cells can be labeled with [2-$H^3$] mannose and cell lysates extracted with chloroform/methanol (3:2) and chloroform/methanol/water (10:10:3) to collect Dol-P-Man and lipid linked oligosaccharides, respectively.

Aliquots containing Dol-P-Man can be subjected to thin layer chromatography while the lipid linked oligosaccharides can be separated by HPLC. Eluate fractions can be analyzed by liquid scintillation counting. Mannose phosphates and GDP-mannose can be separated by descending paper chromatography and [2-$^3$H] mannose released from each fraction by mild acid hydrolysis and measured. The values derived from cells treated with 2-DG or 2-FM can be compared to untreated controls to demonstrate the effects of these drugs on N-linked oligosaccharide precursors and mannose derivatives. Because exogenous mannose reverses 2-DG toxicity, one can also test whether mannose also reverses the 2-DG glycosylation perturbations observed.

In addition to 2-DG and 2-FM, two other glycosylation inhibitors, tunicamycin and deoxymannojirimycin (DMJ), which can inhibit specific steps of N-linked glycosylation, can be used as positive controls. Tunicamycin interferes with the addition of the first N-acetylglucosamine residue onto dolichol pyrophosphate, and DMJ is a specific inhibitor of mannosidase I, which trims 3 mannose residues at the end of the N-linked oligo-saccharide chain. Thus, exogenous mannose should not be able to reverse either the toxicity or the effects on glycosylation of either of these agents. Moreover, because the glucose analog 2-FG does not kill SKBR3 and NSCLC cells under normoxia but is more potent than 2-DG in blocking glycolysis and killing hypoxic cells, it can interfere with glycolysis without affecting glycosylation and so can be used as a tool in such testing as well.

Interference with the process of N-linked glycosylation in the endoplasmic reticulumn (ER) causes improper folding of glycoproteins, which elicits an ER stress response called the unfolded protein response (UPR). Reminiscent of the P53 response to DNA damage, the ER responds to stress in much the same way by (1) increasing folding capacity through induction of resident chaperones (GRP 78 and GRP 94), (2) reducing its own biosynthetic load by shutting-down protein synthesis, and (3) increasing degradation of unfolded proteins. If the stress cannot be alleviated, apoptotic pathways are initiated and the cell subsequently dies. Thus, one measurement of interference with glycosylation is upregulation of UPR.

When SKBR3 cells are treated with 2-DG, both of these ER stress response proteins, GRP 78 and 94, increase as a function of increasing dose; mannose reverses this induction. 2-FG does not induce these proteins. Accordingly, in another embodiment of this invention, this response is used to determine if a tumor or cancer cell is susceptible to treatment in accordance with the present method. Cell lines that are not sensitive to 2-DG under normoxic conditions can be similarly used as negative controls in which the absence of upregulation of these proteins correlates with their resistance to 2-DG.

When ER stress cannot be overcome, apoptotic signals are initiated. ER stress induces a mitochondrial dependent apoptotic pathway via CHOP/GADD153, a nuclear transcription factor that down-regulates BCL-2, and a mitochondrial independent pathway by caspases 4 and 5 in human and caspase 12 in mouse cell lines. Thus, experiments can be performed to determine whether the apoptotic signals particular to ER stress are activated in 2-DG sensitive but not resistant cells. Up-regulation of CHOP/GADD153 and activation of caspases 4 and 5 can be assayed by western blot. As with the previous tests, if this up-regulation is specific to 2-DG-sensitive lines, then the up-regulation observed in a test cancer cell serves as an indicator that the cancer from which the cell was derived is susceptible to treatment in accordance with the present invention.

Because SKBR3 abundantly expresses the glycoprotein ErbB2, it is expected that 2-DG would affect the N-linked glycosylation of this protein, leading to mis-folding and degradation. Western blots of ErbB2 from SKBR3 cells treated with 2-DG can be compared to those from untreated cells to determine the overall level of this protein. Furthermore, the mannose content of ErbB2 following 2-DG treatment can be analyzed by immuno-precipitating this protein and blotting with Conconavalin A, a lectin that recognizes high mannose type N-linked oligosaccharides. Because it is likely that mannose analogs can inhibit the mannose content of not only ErbB2, but all N-linked glycoproteins, whole cell lysates obtained from these cells can also be probed with this lectin. Ponceau stain, which binds to all proteins, can be used as a negative control to verify that 2DG and 2FM specifically affects glycoproteins, and again, this or similar methodology can be used to determine if a cancer or tumor cell is susceptible to treatment in accordance with the present invention.

Even if ER stress indicative of interference with N-linked glycosylation is indeed confirmed to occur by 2-DG and 2-FM, interference with O-glycosylation, which takes place in the cytoplasm as opposed to the ER, can also be evaluated. The scientific literature reports that 2-DG can inhibit the trimming of N-acetylglucosamine residues from an O-glycosylated transcription factor, Sp1, resulting in inhibition of binding to its respective promoters. Sp1 is an important transcription factor for activating numerous oncogenes, which if affected by 2-DG could, at least in part, explain why SKBR3 cells growing under normoxia are sensitive to 2-DG. Thus, the glycosylation pattern of Sp1 following treatment with 2-DG and 2-FM can be investigated by immunoprecipitating and probing with WGA, a lectin that specifically binds O-glycosylated proteins. To the extent that 2-DG affects Sp1 and O-linked glycosylation, this alteration of glycosylation can be measured and used as an indicator that a tumor or other cancer cell line is susceptible to 2-DG-mediated cell killing.

The cell death triggered by the unfolded protein response, which occurs in the endoplasmic reticulum of every cell in response to misfolded proteins, can be enhanced by administration of an additional agent, versipelostatin. Thus, in one embodiment 2-DG, 2-FM, and/or 2-CM is administered to a patient in need of treatment for cancer, and versipelostatin is co-administered to the patient.

Similarly, the cell death that occurs in response to misfolding of proteins can be enhanced by blocking the proteolysis of the misfolded glycoproteins with a proteosome inhibitor. Thus, in another embodiment, the invention provides a method of treating cancer by administering a proteosome inhibitor in combination with 2-DG, 2-FM, and/or 2-CM. In one embodiment, the proteosome inhibitor is Velcade.

Certain types of cancers may be more susceptible to treatment with the present method than others. To identify such types, one can examine a variety of cell types in accordance with the methods of the invention. For example, one can obtain a variety of cancer cell lines from the ATCC and screen them as described above to identify other cell types exquisitely sensitive to mannose analogs, such as 2DG and 2FM, in the presence of oxygen. Cells that are killed in concentrations of 5 mM 2-DG or 2-FM or less are identified as susceptible. These susceptible tumor cell lines can also be tested for their sensitivity to 2-FG and oxamate at doses up to 20 mM and 30 mM, respectively. If interference with glycosylation is the mode of toxicity of 2-DG and 2-FM, then these cell lines should be resistant to the other glycolytic inhibitors, 2-FG and oxamate, unless they have a deficiency in mitochondrial oxidative phosphorylation. To confirm the mitochondrial functionality of these cells, respiration can be measured using, for example, a Clark electrode apparatus. To confirm that toxicity of 2-DG and 2-FM is due to interference with glycosylation in these cell lines, recovery of the cell death by mannose can be assayed as described above.

The molecular basis for one cell being resistant to the current method and another not may be due to difference in the expression of the gene involved in the synthesis of GDP-mannose from glucose i.e. phosphoglucose isomerase (PMI), which converts glucose-6-phosphate to mannose-6-phosphate (see FIG. 7). A deletion in PMI, as mentioned above, was shown to cause glycosylation syndrome 1b, which resulted in hypoglycosylation of serum glycoproteins leading to thrombosis and gastrointestinal disorders in a patient identified with this defect. Addition of mannose to the diet was shown to alleviate the patient's symptoms as well as normalize his glycoproteins. Thus, a deficiency or down-regulation of this enzyme could explain the toxicity of 2DG and 2FM and reversal by exogenous mannose in the sensitive cell lines so far tested.

The reason why down-regulation or deletion of PMI could lead to 2-DG toxicity in the sensitive cell lines is that, in the absence of this enzyme, cells are dependent on exogenous mannose (present in serum) to synthesize N-linked oligosaccharide precursors. Mannose concentrations in the serum of mammals (50-60 μg/ml), or in the medium used for in vitro studies, are known to be significantly less than the concentration of glucose. Thus, in cells with deleted or down-regulated PMI, low doses of 2-DG and 2-FM could favorably compete with the low amounts of mannose present in serum, resulting in complete blockage of the addition of this sugar onto the oligosaccharide chains. On the other hand, cells with normal PMI can produce GDP-mannose from glucose; thus, much higher doses of 2-DG or 2-FM are necessary to cause complete disruption of oligosaccharide assembly. This could explain why most cells tested are resistant to 2DG under normoxic conditions. Direct measurements of the activity of this enzyme can be used in accordance with the invention to determine whether defective or low PMI levels are responsible for the sensitivity to 2-DG and 2-FM in select cells growing under normoxia, and if so, then can be used to identify tumor and cancer cells susceptible to treatment in accordance with the present method. Another, but less likely, possibility to explain this unusual sensitivity, is that the PMI in these select cells is inhibited more by 2-DG and 2-FM than in the majority of normal and tumor cell lines that are unaffected by these agents when growing under normal oxygen tension. In order to test this directly, cell extracts can be isolated from SKBR resistant and sensitive cell pairs and the ability to convert glucose-6-P to mannose-6-P can be determined in the presence or absence of 2-DG and 2-FM.

If decreased PMI activity is not responsible for 2-DG toxicity in SKBR3 sensitive cells, then an alternative mechanism to explain this is up-regulation of genes that encode enzymes involved in the production of mannose derivatives used for oligosaccharide assembly, i.e. phosphomannomutase (PMM) and GDP-Man synthase (FIG. 7). The possibility exists that cells sensitive to 2-DG are undergoing increased glycosylation and therefore up-regulate either one or both of these enzymes. Such a cell would accumulate more 2-DG-GDP, therefore leading to greater interference with glycosylation and consequently cell death than a resistant cell in which glycosylation was occurring at a slower rate or capacity.

Regardless of whether up-regulation of glycosylation turns out to be a mechanism by which cells become sensitive to 2-DG, the total amount of 2-DG that is accumulated or incorporated into a cell also contributes to its increased sensitivity. Thus, uptake and accumulation studies using [$^3$H] labeled 2-DG can be performed determine if a cell higher levels of glucose transporter, rendering it more susceptible to treatment in accordance with the present method.

One can obtain 2-DG resistant mutants from sensitive cells by treating the latter with increasing doses of 2-DG and selecting for survival. Resistant mutants and their parental sensitive counterparts can be used in the methods described. Such studies should also provide a means of understanding mechanisms by which cells become resistant to 2-DG and therefore may be applicable to better use of this drug clinically.

The foregoing discussion reflects that a molecular signature can be used to predict which tumor cell types will be sensitive to 2-DG and 2-FM in the presence of oxygen.

Execution of cell death shows a remarkable plasticity spanning the range between apoptosis and necrosis. Using established methods to compare the mode of cell death by investigating the type of DNA cleavage, changes in membrane composition, integrity, and tone can determine the mechanisms of cell death induced by interference with glycosylation and by inhibition of glycolysis. Inhibition of both glycolysis and oxidative phosphorylation results in severe ATP depletion, thereby causing a switch from apoptosis to necrosis. Because ATP is required to activate caspases, when it is severely depleted, apoptosis is blocked, and eventually, without energy, the cell succumbs via necrosis. An aerobic cell treated with a glycolytic inhibitor is able to produce ATP via oxidative phosphorylation fueled by either amino acids and or fats as energy sources. Thus, when 2-DG induces a UPR response leading to cell death under normoxia, it is believed that cells will undergo apoptosis. Conversely, in hypoxic cell models, it is expected that when the dose of 2-DG is high enough to block glycolysis, these cells should undergo ATP depletion and die through necrosis.

One can therefore use established methods of assaying for apoptosis and necrosis and determine whether 2-DG is killing cells via apoptosis, necrosis and or a mixture of both. Several apoptotic parameters can be assayed to distinguish necrosis from apoptosis by using flow cytometry analysis. Following 2-DG treatment, cells can be dual-stained with Annexin-V and propidium iodide to detect exposure of phosphatidyl serine on the cell surface and loss of cell membrane integrity, respectively. Staining with either annexin-V alone or both annexin-V and propidium iodide indicates apoptosis, while staining with propidium iodide alone indicates necrosis. Furthermore, two of the final outcomes of apoptosis, nuclear DNA fractionation and formation of single stranded DNA, can also be measured. These two latter parameters have been reported to be unique to apoptotic cell death and have been used by various investigators to differentiate apoptosis from necrosis. ATP levels can also be assayed to determine whether they correlate with the modes of death detected.

Moreover, if 2-DG induces both apoptosis and necrosis in hypoxic cells, then one can determine the mode of cell death induced by 2-FG under hypoxic conditions. As mentioned above, 2-FG does not interfere with glycosylation and is a more potent glycolytic inhibitor than 2-DG. Thus, it is expected that the cell death induced by 2-FG will occur solely via necrosis.

Cell lines proven to be sensitive to 2DG and/or 2FM and/pr 2-CM in vitro under normoxia that grow readily in nude mice can be used to demonstrate that 2DG (and 2-FM and 2-CM) is effective as a single agent against them when given in vivo. After tumors reach a certain size, treatment with 2DG will be applied via intraperitoneal injection. Dose and treatment regimen of 2DG according to the minimal lethal dose established previously in these animals can be used to demonstrate tumor regression and cytotoxicity.

Reference will now be made to specific examples illustrating the constructs and methods above. It is to be understood that the examples are provided to illustrate preferred embodiments and that no limitation to the scope of the invention is intended thereby.

EXAMPLES

Example 1

Materials and Methods

Isolation of resistant mutants. 2-DG sensitive SKBR3 and NSCLC cells were exposed to increasing doses of 2-DG and resistant colonies were isolated and cloned at the appropriate doses of 2-DG. The cloned 2-DG resistant cells were then analyzed and compared to the wild-type sensitive counterpart for expression of specific genes that may be responsible for this unique sensitivity.

Drugs and antibodies. Rho 123, oligomycin, staurosporin, and 2-DG, 2-FG, 2-FM, tunicamycin, deoxymannojirinomycin were obtained from Sigma Chemical Co. The following primary Abs can be used: monoclonals to HIF-1a and LDH-a.

(BD Biosciences); erbB2 (Calbiochem, USA); Grps 78 & 94, (StressGen, USA); caspases 4 and 5 (StressGen, USA); and actin (Sigma Chemical Co.); polyclonal abs to GLUT-1 (USA Biological) and GADD153/CHOP (Santa Cruz, USA). The secondary antibodies were horseradish peroxidase conjugated rabbit anti-mouse and goat anti-rabbit (Promega, Co.).

Cytotoxicity assay and Rapid DNA Content Analysis. Cells were incubated for 24 hr at 37° C. in 5% $CO_2$ at which time drug treatments began and were continued for 72 hr. At this time, attached cells were trypsinized and combined with their respective culture media followed by centrifugation at 400 g for 5 min. Pellets containing the cells were either resuspended in 1.5 ml of a medium/trypan blue mixture for cytotoxicity assays or propidium iodide/hypotonic citrate staining solution for determining the nuclear DNA content and cell cycle by a Coulter XL flow cytometer. A minimum of 10,000 cells were analyzed to generate a DNA distribution histogram.

Lactic acid assay. Lactic acid was measured by adding 0.025 ml of deproteinated medium, from treated or non-treated cultures, to a reaction mixture containing 0.1 ml of lactic acid dehydrogenase (1000 units/ml), 2 ml of glycine buffer (glycine, 0.6 mol/L, and hydrazine, pH 9.2), and 1.66 mg/ml NAD. Deproteinization occurred by treating 0.5 ml of medium from test cultures with 1 ml of perchloric acid at 8% w/v, vortexing for 30 s, then incubating this mixture at 4° C. for 5 min, and centrifuging at 1500 g for 10 min. The supernatant was centrifuged three times more, and 0.025 ml of a final clear supernatant was used for lactic acid determinations. Formation of NADH was measured with a Beckman DUr 520 UV/vis spectrophotometer at 340 nm, which directly corresponds to lactic acid levels as determined by a lactate standard curve.

2-DG uptake. Cells were seeded into Petri dishes and incubated for 24 hr at 37° C. and 5% $CO_2$. The medium was then removed and the plates were washed with glucose- and serum-free medium. 2 ml of serum-free medium containing $^3H$ labeled 2-DG were added to the dish (1 µCi/plate), and the plates were incubated for the appropriate amount of time. The medium was then removed, the plates were washed three times with at 4° C., and serum-free medium containing 100 µM of unlabeled 2-DG, and 0.5 ml of 1N NaOH was added. After incubating at 37° C. for 3 hr (or overnight), the cells were scraped and homogenized by ultrasonication (10 seconds). The solution was collected into tubes for $^3H$ quantification (saving a portion for protein assay). 100 µL of formic acid, 250 µL of sample, and 7 ml of scintillation cocktail were combined in a $^3H$ counting vial and read with a scintillation counter. Transport rate (nmol/mg protein/time) was calculated by Total CPM/Specific Radioactivity/Total Protein.

ATP quantitation assay. The ATP lite kit (Perkin Elmer) can be used to quantify levels of ATP. About 50 µL of cell lysis solution were added to 100 µL of cell suspension in a white-bottom 96-well plate. The plate was incubated at room temperature on a shaker (700 rpm) for five minutes. 50 µL of substrate solution was then added to the wells and shaken (700 rpm) for another five minutes at room temperature. The plate was then dark adapted for ten minutes and measured for luminescence.

Metabolic labeling and extraction of Dol-P-Man and lipid linked oligosaccharides (LLO). According to the procedure described by Lehle, cells were labeled with [2-$^3H$] mannose for 30 min, scraped into 2 ml of ice-cold methanol and lysed by sonication. After adding 4 ml of chloroform, the material was sonified, followed by centrifugation for 10 min at 5000 rpm at 4° C. Supernatants were collected and the pellets extracted twice with chloroform/methanol (3:2) (C/M). The combined supernatants containing Dol-P-Man and lipid linked oligosaccharides of small size were dried under $N_2$, dissolved in 3 ml of C/M, washed, and analyzed by thin layer chromatography on Silica gel 60 aluminium sheets in a running buffer containing $C/M/H_2O$ (65:25:4). The remaining pellet containing the large size LLOs was washed and extracted with $C/M/H_2O$ (10:10:3). Corresponding aliquots of the C/M and $C/M/H_2O$ extracts were combined and dried under $N_2$ and resuspended in 35 µl 1-propanol. To release the oligosaccharides by mild acid hydrolysis, 500 µl 0.02 N HCl were added followed by incubation for 30 min at 100° C.

The hydrolyzed material was dried under $N_2$ and then resuspended by sonification in 200 µl of water and cleared by centrifugation. The supernatant containing the released oligosaccharides were used for HPLC analysis.

Size fractionation of oligosaccharides by HPLC. The separation of LLOs can be performed on a Supelcosil LC-$NH_2$ column (25 cm×4.6 mm; 5 µm; Supelco) including a LC-$NH_2$ (2 cm×4.6 mm) precolumn. A linear gradient of acenonitrile from 70% to 50% in water was applied at a flow rate of 1 ml/min. Eluate fractions were analyzed by liquid scintillation counting.

Preparation of mannose 6-phosphate, mannose 1-phosphate, GDP-mannose. After labeling with [2-$^3H$] mannose, cells were harvested and free mannose was separated from nucleotide linked and phosphorylated mannose derivatives by paper chromatography as described by Korner et al. Eluate fractions were analyzed by liquid scintillation counting.

Western Blot analysis. Cells were plated at $10^4$ cell $cm^{-2}$ and grown under drug treatment for the indicated times. At the end of the treatment period, cells were collected and lysed with RIPA buffer (150 mM NaCl, 1% Np-40, 0.5% DOC, 0.1% SDS, 50 mM Tris-HCl, ph 8.0) supplemented with a proteinase inhibitor cocktail. DNA was fragmented by passing the solution through a 21 G needle 10 times. Protein concentrations were measured by a Super Protein Assay kit (Cytoskeleton, USA). Samples were mixed with 2× Laemmli sample buffer (Bio-Rad, USA) and run on a SDS-polyacrylamide gel. Gels were transferred to nitrocellulose membranes (Amersham, USA) and probed with specific antibodies. Following probing, membranes were washed and incubated with an HRP conjugated secondary antibody. Chemiluminesence was detected by exposure to film.

Where indicated, membranes were stripped with Stripping Buffer (Pierce, USA) and reprobed with anti-actin primary antibody.

Immunoprecipitation of ErbB2. Following treatment of cells for 24 hours, they were lysed by RIPA (15 mM NaCl, 1% Np-40, 0.1% SDS) and sonicated. Cell lysates were incubated with CnBr activated Sepharose beads (Amersham, USA) linked to monoclonal ErbB2 antibody (Calbiochem, USA) and spun at 400 g for 5 min. Immunoprecipitated ErbB2 was loaded onto SDS-PAGE gels and blotted with Conconavalin A, which binds specifically to mannose residues of glycoproteins.

Apoptosis assay. The apoptosis ELISA assay was used as described and is based on selective DNA denaturation in condensed chromatin of the apoptotic cells by formamide and reactivity of single-stranded DNA (ssDNA) in apoptotic cells with monoclonal antibodies highly specific to ssDNA. These antibodies specifically detect apoptotic cells and do not react with the necrotic cells.

Investigation of cell death mechanism by flow cytometry. Apoptosis was distinguished from necrosis by An-nexin-V-Fluos Staining kit (Roche, USA). Following indicated treatments, $10^6$ cells were resuspended in incubation buffer containing FITC conjugated Annexin-V and propidium iodide to detect phosphotdylserine and plasma membrane integrity, respectively. After incubation, cells were analyzed by a flow cytometer using 488 nm excitation and a 515 nm bandpass filter for fluorescein detection and a filter >600 nm for PI detection.

Gene expression profiling. A Gene-array kit can be purchased from Super Array Inc. Total RNA from selected cell-lines was probed with dCTP.[-$^{32}$P] (3000 Ci/mmol) through a reverse transcription reaction. The labeled cDNA probed was then added to pre-hybridized array membrane and incubated in a hybridization oven overnight. After multiple washings to remove free probe, the membrane was exposed to X-ray film to record the image.

In vivo tumor experiments. The protocol described for 2-DG+Dox reported in *Cancer Res.* 2004 (by Lampidis et al.) can be replicated substituting 2-FG for 2-DG. Nude mice, strain CD1, 5 to 6 weeks of age, weighing 30 g, were implanted (S.C.) with 100 µl of human osteosarcoma cell line 143b at $10^7$ cells/ml. When tumors are 50 mm$^3$ in size (9-10 days later), the animals were pair-matched into four groups (8 mice/group) as follows: saline-treated control; 2-FG alone; Dox alone; and Dox+2-FG. At day 0, the 2-FG alone and Dox+2-FG groups received 0.2 ml of 2-FG i.p. at 75 mg/ml (500 mg/kg), which was repeated 3× per week for the duration of the experiment. On day 1, the Dox and Dox+2-DG groups received 0.3 ml of Dox i.v. at 0.6 mg/ml (6 mg/kg), which was repeated once per week for a total of three treatments (18 mg/kg). Mice were weighed, and tumor measurements were taken by caliper three times weekly.

SKBR3 cells were implanted and tested in the above model with 2-DG or 2-FM without doxorubicin (Dox).

Example 2

Normoxic Sensitivity of Certain Tumor Cells to Mannose Derivatives

Cells growing under hypoxia are solely dependent on glucose metabolism via glycolysis for energy production. Consequently, when this pathway is blocked, with 2-deoxy-D-glucose (2-DG), hypoxic cells die. In contrast, when glycolysis is blocked under normoxia most cells survive, because fats and proteins can substitute as energy sources to fuel mitochondrial oxidative phosphorylation. The invention is based in part on the discovery that, under normal oxygen tension, a select number of tumor cell lines are killed at a relatively low dose of 2-DG (4 mM). It has been shown previously that 2-DG interferes with the process of N-linked glycosylation in viral coat glycoprotein synthesis, which can be reversed by addition of exogenous mannose. Because the 2-DG toxicity under normoxia described herein can be completely reversed by low dose mannose (2 mM), glycosylation and not glycolysis is believed to be the mechanism responsible for these results. Additionally, 2-fluoro-deoxy-D-glucose (2-FDG), which is more potent than 2-DG in blocking glycolysis and killing hypoxic cells, shows no toxicity to any of the cell types that are sensitive to 2-DG under normoxic conditions.

To investigate the effect of 2-DG on glycoprotein synthesis, concanavalin A (which specifically binds to mannose moieties on glycoproteins) was used in studies that showed that 2-DG but not 2-FDG decreased binding, which was reversible by addition of exogenous mannose. Similarly, the unfolded protein response (UPR) proteins, grp 98 and 78, which are known to be induced when n-linked glycosylation is altered, were found to be upregulated by 2-DG but not 2-FDG, and again, this effect could be reversed by mannose. Moreover, 2-DG induces cell death via upregulation of a UPR specific transcription factor (GADD154/CHOP), which mediates apoptosis. Thus, in certain tumor cell types, 2-DG can be used clinically as a single agent to kill selectively both the aerobic (via interference with glycosylation) as well as the hypoxic (via inhibition of glycolysis) cells of a solid tumor.

Despite angiogenesis, the metabolic demands of rapid tumor growth often outstrip the oxygen supply, which contributes to formation of hypoxic regions within most solid tumors. The decrease in oxygen levels that occurs as the tumor grows, leads to slowing the replication rate of cells in the hypoxic portions, resulting in resistance to most chemotherapeutic agents which normally target rapidly proliferating cells (1; see the list of references cited at the end of this Example). Hypoxic cells are also resistant to radiation treatment due to slow growth and the absence of oxygen necessary to produce reactive oxygen species (2). In addition to these disadvantages for cancer treatment, hypoxia renders a tumor cell dependent on glycolysis for energy production and survival. Under hypoxia, oxidative phosphorylation, the most efficient means of ATP production, is inhibited, leaving glycolysis as the only means for producing ATP. Thus, blocking glycolysis in hypoxic tumor cells should lead to cell death. Indeed, under 3 different conditions of simulated hypoxia in vitro, it has been shown that tumor cells can be killed by inhibitors of glycolysis (3). Moreover, inhibition of glycolysis in normally oxygenated cells does not significantly affect their energy production, because alternative carbon sources, i.e. amino acids and fats, can be utilized to drive mitochondrial oxidative phosphorylation. Therefore, glycolytic inhibitors can be used to target hypoxic tumor cells selectively, without showing much toxicity to normal or tumor cells growing aerobically (4,5).

In fact, in vivo experiments have shown that 2-DG (targeting slow-growing hypoxic tumor cells) increases the efficacy of standard chemotherapeutic agents (directed against rapidly proliferating aerobic cells) in different human tumor xenografts (6). The results of these studies as well as data from in vitro models of hypoxia (3) has led to testing this strategy for improving chemotherapy protocols in humans in the form of a Phase I clinical trial entitled "A Phase I dose escalation trial of 2-deoxy-D-glucose alone and in combination with docetaxel in subjects, with advanced solid malignancies," which is currently ongoing. The data from animal studies, as well as the preliminary results from the Phase I clinical trial, indicate that 2-DG is well-tolerated and relatively non-toxic to normal cells.

Although theoretically tumor cells with mitochondria able to undergo oxidative phosphorylation should not be killed by the glycolytic inhibitor 2-DG, a select number of cancer cell lines die in the presence of oxygen with low doses of this sugar analog. The mechanism of toxicity is not via blockage of glycolysis, because these cell lines undergo normal mitochondrial respiration and are resistant to other glycolytic inhibitors. A similar mechanism has been shown in viral glycoprotein synthesis, in which 2-DG blocks N-linked glycosylation by interfering with lipid linked oligosaccharide assembly (7,8). The toxicity with 2-DG in the select tumor cell lines growing under normoxia appears to be due to a similar mechanism.

In accordance with the invention, 2-DG can be used as a single agent in certain patients with solid tumors containing cells sensitive to 2-DG under normoxia. Thus, in these patients 2-DG should have a dual effect by (1) targeting the aerobic tumor cell population via interference with glycosylation; and (2) inhibiting glycolysis in the hypoxic portion of the tumor; both mechanisms lead to cell death.

Materials and Methods

Cell types. The $\Delta^0$ cells were isolated by treating osteosarcoma cell line 143B (wt) with ethidium bromide for prolonged periods, as previously described (9). Because the $\Delta^0$ cells are uridine and pyruvate auxotrophs, they were grown in DMEM (GIBCO, USA) supplemented with 10% fetal calf serum, 50 µg/ml of uridine and 100 mM sodium pyruvate. The SKBR3 cell line was obtained from Dr. Joseph Rosenblatt's laboratory at the University of Miami. The pancreatic cancer cell lines 1420 and 1469, the ovarian cancer cell line SKOV3, the cervical cancer cell line HELA, and the osteosarcoma cell line 143B were purchased from ATCC. The non-small cell lung cancer and small cell lung cancer cell lines were derived from patients by Dr. Niramol Savaraj at the University of Miami. SKBR3 and SKOV3 cells were grown in McCoy's 5A medium; 1420, 1469 and 143B were grown in DMEM (GIBCO, USA); and HELA was grown in MEM (GIBCO, USA). The media was supplemented with 10% fetal bovine serum. All cells were grown under 5% $CO_2$ and 37° C.

Drugs and chemicals. 2-DG, oligomycin and tunicamycin were purchased from Sigma. 2-FDG and 2-FDM were a kind gift of Dr. Priebe (MD Anderson Cancer Center, TX).

Hypoxia. For studies in hypoxic conditions (Model C), cells were seeded and incubated for 24 hr at 37° C. and 5% $CO_2$ as described below for direct cytotoxicity assays. After the 24 hr incubation, cells received drug treatment and were placed in a Pro-Ox in vitro chamber attached to a model 110 oxygen controller (Reming Bioinstruments Co. Redfield, N.Y.) in which a mixture of 95% Nitrogen and 5% $CO_2$ is used to perfuse the chamber to achieve the desired $O_2$ levels (0.1%).

Cytotoxicity assay. Cells were incubated for 24 hr at 37° C. in 5% $CO_2$ at which time drug treatments began and continued for 72 hr. At this time, attached cells were trypsinized and combined with their respective culture media followed by centrifugation at 400 g for 5 min. The pellets were resuspended in 1 ml of Hanks solution and analyzed by Vi-Cell (Beckman Coulter, USA) cell viability analyzer.

Lactic acid assay. Lactic acid was measured by adding 0.025 ml of deproteinated medium, from treated or nontreated cultures, to a reaction mixture containing 0.1 ml of lactic dehydrogenase (1000 units/ml), 2 ml of glycine buffer (glycine, 0.6 mol/L, and hydrazine, pH 9.2), and 1.66 mg/ml NAD. Deproteinization occurred by treating 0.5 ml medium from test cultures with 1 ml of perchloric acid at 8% w/v, vortexing for 30 s, then exposing this mixture to 4° C. for 5 min, and centrifugation at 1500 g for 10 min. The supernatant was centrifuged three times more, and 0.025 ml of a final clear supernatant were used for lactic acid determinations as above. Formation of NADH was measured with a Beckman DUr 520 UV/vis spectrophotometer at 340 nm, which directly corresponds to lactic acid levels as determined by a lactate standard curve.

ATP quantification assay. The ATP lite kit (Perkin Elmer) can be used to quantify levels of ATP. About 50 ml of cell lysis solution were added to 100 ml of cell suspension in a white-bottom 96-well plate. The plate was incubated at room temperature on a shaker (700 rpm) for five minutes. About 50 ml of substrate solution were then added to the wells and shaken (700 rpm) for another five minutes at room temperature. The plate was then dark adapted for ten minutes and measured for luminescence. To normalize the reduction of ATP production to growth inhibition which results due to treatment with 2-DG or 2-FDG, parallel experiments were run to measure the total protein concentration using a microBCA protein detection kit (Pierce, Rockford, Ill.).

Western Blot analysis. Cells were plated at $10^4$ cell $cm^{-2}$ and grown under drug treatment for the indicated times. At the end of the treatment period, cells were collected and lysed with 1% SDS in 80 mM Tris-HCL (ph 7.4) buffer supplemented with a proteinase inhibitor cocktail. DNA was fragmented by sonication and protein concentrations were measured by microBCA protein assay kit (Pierce, USA). Samples were mixed with 2× Laemmli sample buffer (Bio-Rad, USA) and run on a SDS-polyacrylamide gel. Gels were transferred to nitrocellulose membranes (Amersham, USA) and probed with anti-KDEL (Stressgen, Canada) (for Grp78 and Grp94); polyclonal anti-CHOP/GADD154 (Santa Cruz, USA), polyclonal anti-erbB2 (DAKO, USA). Following probing, membranes were washed and incubated with an HRP conjugated secondary antibody. Chemiluminesence was detected by exposure to film. Where indicated, membranes were stripped with Stripping Buffer (Pierce, USA) and reprobed with anti-actin (Sigma, USA) primary antibody. To analyze conconavalin A (ConA) binding, the membranes were incubated with 0.2 µg/ml HRP-conjugated ConA, and chemiluminescence was detected as described.

Oxygen consumption. Cells were grown in 75 $cm^2$ flasks until they were 70-80% confluent followed by trypsinization and counting. $5 \times 10^6$ cells were resuspended in 1 ml of DMEM which does not contain glucose or fetal bovine serum. Oxygen consumption was measured by Clark electrode (Hansatech, Cambridge, UK) for 10 min and than 2 µM of potassium cyanide was added to respiratory medium in order to directly calculate the amount of oxygen utilized by the mitochondrial respiratory chain.

Three in vitro models of hypoxia. We previously characterized three models of anaerobiosis as follows: Model A are tumor cells treated with 0.05 µg/ml of oligomycin (a mitochondrial inhibitor of ATP synthase); Model B are cells that are deficient in mitochondrial DNA and Model C are cells treated in an hypoxic (0.5% $O_2$) chamber (Reming Bioinstruments, Redfield, N.Y.).

Results

2-DG and 2-fluoro-D-mannose, but not 2-FDG, Kill SKBR3 Cells Growing Under Normoxic Conditions In surveying a number of tumor cell lines for their differential sensitivity to glycolytic inhibitors under normoxic vs hypoxic conditions, it was discovered that the human breast cancer cell line SKBR3 was sensitive to 2-DG when grown under normoxic conditions. FIGS. 1A and B demonstrate that when SKBR3 is treated with 3 mM of 2-DG for 72 hrs, 50% of its growth is inhibited ($ID_{50}$), while at 12 mM 60% of the cells are killed. Previous studies showed that when mitochondrial respiration is deficient or chemically blocked, tumor cells die when treated with similar doses of 2-DG. Therefore, to determine whether these cells were deficient in mitochondrial respiration, their oxygen consumption was measured. As demonstrated in Table 1 below, there was no significant difference between the average oxygen consumption of SKBR3 cells and two other cell lines that are resistant to 2-DG treatment when grown under normoxic conditions. On the other hand, a mitochondrial deficient cell line, $\Delta^0$ showed drastically reduced oxygen consumption, confirming that SKBR3 was respiring normally. Furthermore, two other cell lines, 1420 and HELA, which were sensitive to 2-DG under normoxia, respired as well or better than the resistant cell lines (see Table 1). Thus, the toxicity of 2-DG in these cells under normoxic conditions is due to a mechanism other than blockage of glycolysis. To confirm this, SKBR3 cells were treated with two other glycolytic inhibitors i.e. 2-deoxy-2-fluoro-glucose (2-FDG) and oxamate. In FIGS. 1A and B, it can be seen that neither of these agents caused toxicity to SKBR3 cells when grown under normoxia.

TABLE 1

Comparison of oxygen consumption in 2-DG sensitive vs. resistant cell lines

| Cell line | Tissue Type | Average $O_2$ consumption (nmol/$10^6$ cells/min) |
|---|---|---|
| 1436 | osteosarcoma | 2.81 ± 0.11 |
| $A^0$ | osteosarcoma | 0.09 ± 0.004 |
| SKOV3 | ovarian carcinoma | 2.38 ± 0.32 |
| SKBR3 | breast adenocarcinoma | 2.01 ± 0.29 |
| 1420 | pancreatic adenocarcinoma | 4.70 ± 0.03 |
| HELA | cervical adenocarcinoma | 2.76 ± 0.04 |

Moreover, 2-fluoro-D-mannose (2-FDM) was similar to 2-DG, albeit less efficient, in causing cytotoxicity in SKBR3 cells (see FIG. 1). Both 2-DG and 2-FDM but not 2-FDG resemble the structure of mannose and thereby can interfere with the metabolism of mannose. This data indicates that interference by 2-DG and 2-FDM with the metabolism of mannose, which is primarily involved in N-linked glycosylation of numerous proteins, results in cell death as well as growth inhibition in SKBR3 cells.

Figure 2:
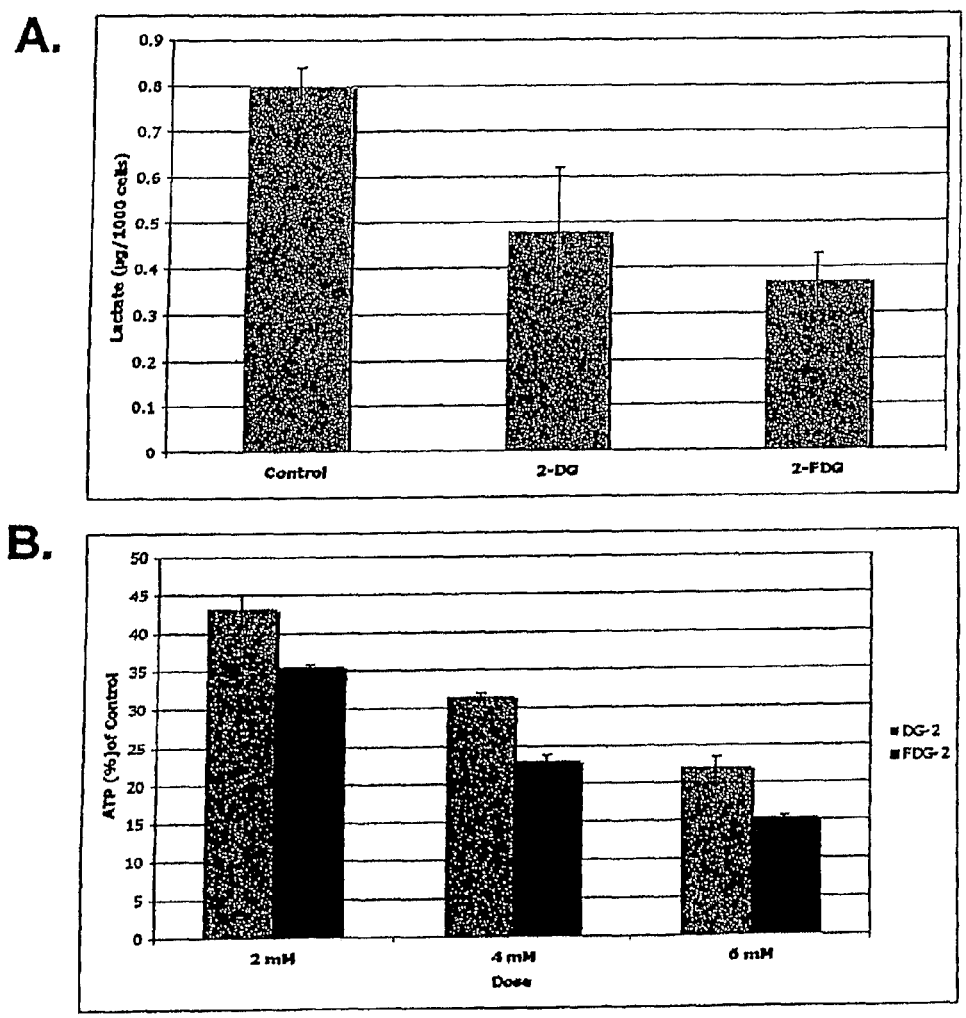
FIG. 2 shows (A) SKBR3 cells were grown for 24 hr in the absence or presence of either 2 mM of 2-DG or 2-FDG and lactate concentration in the medium was measured, and (B) SKBR3 cells were grown for 6 hours in the presence of either 2-DG or 2-FDG at the same concentrations used in (A) followed by quantification of ATP in whole cell lysates.

2-FDG is a Better Inhibitor of Glycolysis than 2-DG Leading to Better Depletion of ATP in SKBR3 Cells In a previous report, it was suggested that the toxicity of 2-DG in SKBR3 cells growing under normoxia was mediated via inhibition of glycolysis and ATP production (10). However, as mentioned above, another glycolytic inhibitor, 2-FDG, is non-toxic in these cells. Moreover, the 2-FDG analog is better than 2-DG in inhibiting glycolysis and killing hypoxic cells (11). Indeed, when SKBR3 cells were treated with 2-FDG vs. 2-DG, the former inhibited lactate levels (a measure of glycolysis) better than the latter (see FIG. 2A). Furthermore, ATP depletion was more prominent with 2-FDG treatment, further confirming that this sugar analog is a better inhibitor of glycolysis and ATP production in these cells (see FIG. 2B). Moreover, it was discovered that, when SKBR3 cells were grown under hypoxic conditions, 2-FDG was more toxic than 2-DG, further confirming that it is a better inhibitor of glycolysis in SKBR3 cells. Thus, in contrast to previous reports, the toxicity induced by 2-DG under normoxic conditions appears to be independent from its ability to inhibit glycolysis and decrease ATP pools.

2-DG Toxicity in SKBR3 Cells Under Normoxia can be Reversed by Exogenous Mannose In viral proteins, 2-DG has been shown to inhibit the assembly of N-linked oligosaccharides, and this inhibition can be reversed by exogenous mannose (7). FIGS. 3A and 3B illustrate that with the addition of mannose, but not other sugars, i.e. glucose, fructose and fucose, cell death from 2-DG exposure under normoxia can be reversed, suggesting that cell death is mediated by interference with glycosylation via a similar mechanism (7). As a negative control, it was found that mannose does not reverse tunicamycin induced toxicity in SKBR3 cells under the same conditions. This can be explained by the fact that tunicamycin interferes with glycosylation at a step preceding the addition of mannose to the oligosaccharide chain, thereby rendering it independent of mannose metabolism.

It is important to note that low doses of mannose (1 mM) were sufficient to completely reverse cell death caused by 4 mM of 2-DG in the presence of higher concentrations of glucose (12 mM). In contrast, 1 mM of additional glucose has no effect on 2-DG toxicity. However, if the concentration of glucose in the medium is drastically increased to 25 mM, cell death induced by 2-DG is partially decreased as expected. Therefore, although the concentration of glucose in the medium is an important factor for the effect of 2-DG, the competition between mannose and 2-DG appears to be the key determinant for the toxicity of this sugar analog in cells growing under normoxia.

2-DG Toxicity in Three Models of 'Hypoxia' Cannot be Reversed by Exogenous Mannose As mentioned above, cells growing under hypoxic conditions depend solely on glycolysis to produce energy. Thus, inhibition of this metabolic pathway by glycolytic inhibitors should lead to cell death, as has been previously demonstrated (3). To distinguish the mechanism by which 2-DG is toxic to SKBR3 cells growing under normoxia, mannose was added to cells growing under three different conditions of 'hypoxia'. No significant difference was found in growth inhibition and cell death in either normal growth medium or in the same medium supplemented with 2 mM mannose. These results provide evidence that the reversal of toxicity of 2-DG in SKBR3 cells growing under normoxia by exogenous mannose is unrelated to the glycolysis, further implicating interference with glycosylation as the mode of cell death in these cells growing under normoxia.

2-DG and 2-FDM are Toxic to Only a Select Number of Tumor Cell Lines Growing Under Normoxic Conditions To investigate whether the toxicity of 2-DG under normoxic conditions was confined to a certain type of cancer tissue, a number of cell lines were tested. The results of this testing, shown in Table 2, show that only a select number of tumor cell lines (6 out of 15) growing under normal oxygen tension undergo significant cell death when treated with either 2-DG or 2-FDM but not 2-FDG at 6 mM. The cell lines that were found to be sensitive to 2-DG were SKBR3, a breast cancer cell line; 1420, a pancreatic cancer cell line; 2 non-small cell lung cancer cell lines derived directly from patients; RT 8226, a multiple myeloma cell line; HELA, a cervical carcinoma and TG98, a glioblastoma cell line. However, cancer cell lines derived from similar tissues were found to be resistant to both 2-DG and 2-FDM under normal oxygen tension, indicating that toxicity of these sugar analogs is not necessarily tissue type specific.

TABLE 2

Resistant vs. sensitive cell lines (2-DG under normoxia)

| 2-DG Sensitive Cell Lines | 2-DG Resistant Cell Lines |
|---|---|
| SKBR3, breast cancer | SKOV3, ovarian cancer |
| 1420, pancreatic cancer | 1469, pancreatic cancer |
| HELA, cervical cancer | 143B, osteosarcoma |
| S-1 & S-2, non-small cell lung cancer | Ra-1, 2 and 3, small cell lung cancer |
| TG98, brain cancer (glioblastoma) | MCF-7, breast cancer |
| RT 8228, multiple myeloma | U266, multiple myeloma |
|  | HEPA-1, rat hepatoma |
|  | MDA-MB-231, breast cancer |
|  | MDA-MB-468, breast cancer |

Figure 4:
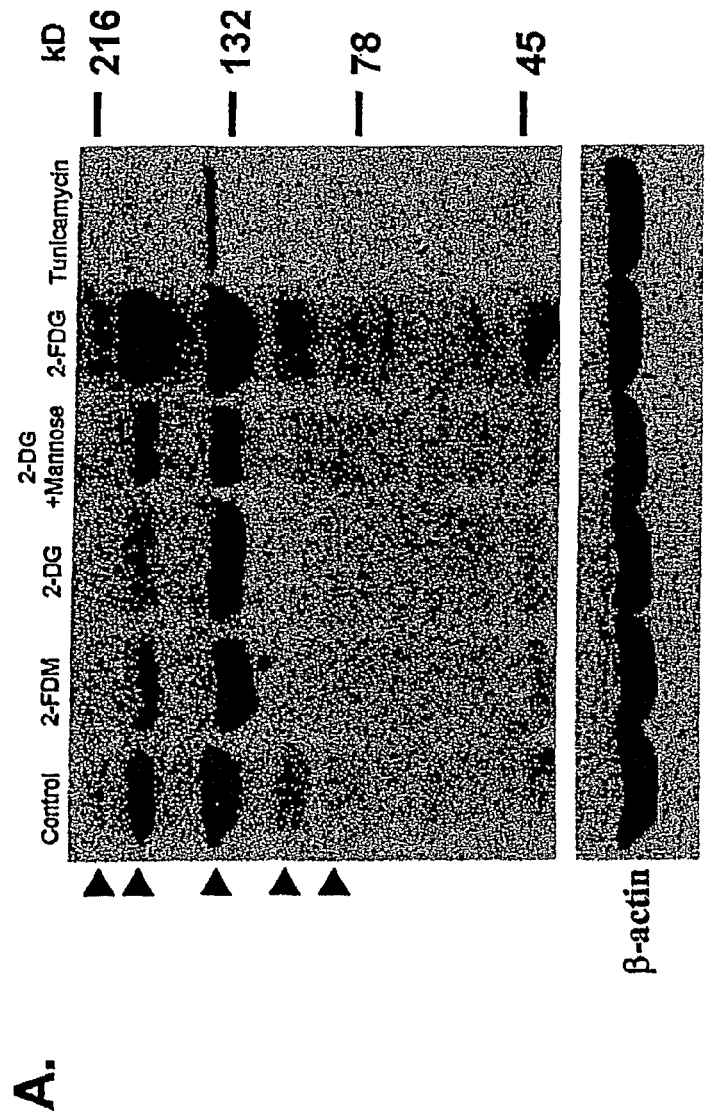
FIG. 4 shows (A) SKBR3 cells were treated for 48 hr with various drugs as indicated for each lane and total cell extracts were obtained and blotted with HRP-conjugated ConA. Equal amounts of protein were loaded in each lane and verified by β-actin. The glycoproteins (demarked by arrows) show that 8 mM of 2-DG and 2-FDM but not 2-FDG decrease their ConA binding and that this reduction can be reversed by mannose. (B) The same cells were blotted for erbB2, a highly expressed glycoprotein. A change in the molecular weight of this protein is caused by similar doses of 2-DG and 2-FDM.
Figure 4:

2-DG and 2-FDM Decrease Conconavalin a (ConA) Binding and the Molecular Weight of a Glycoprotein in SKBR3 Cells ConA is a lectin that specifically binds mannose on glycoproteins and has been used to detect high mannose type glycoproteins (12). This technique was used to show that both 2-DG and 2-FDM as well as tunicamycin decrease ConA binding in a number of glycoproteins (see FIG. 4A). Moreover, exogenous mannose restores control ConA binding levels in 2-DG and 2-FDM but not tunicamycin treated cells, while 2-FDG treated cells show no reduction in ConA binding. Furthermore, change in the size of a known glycoprotein, erbB2, which is a tyrosine-kinase receptor expressed in SKBR3 cells following 2-DG treatment, was analyzed by western blot. FIG. 4B illustrates that both 2-DG and 2-FDM decreased the molecular weight of erbB2, while 2-FDG had no effect. In correlation with the ConA data, exogenous mannose restored the size of the protein to its original weight. These data further support the conclusion that 2-DG and 2-FDM but not 2-FDG are toxic to select tumor cells via interference with N-linked glycosylation, and that this interference can be reversed by mannose.

Figure 5:
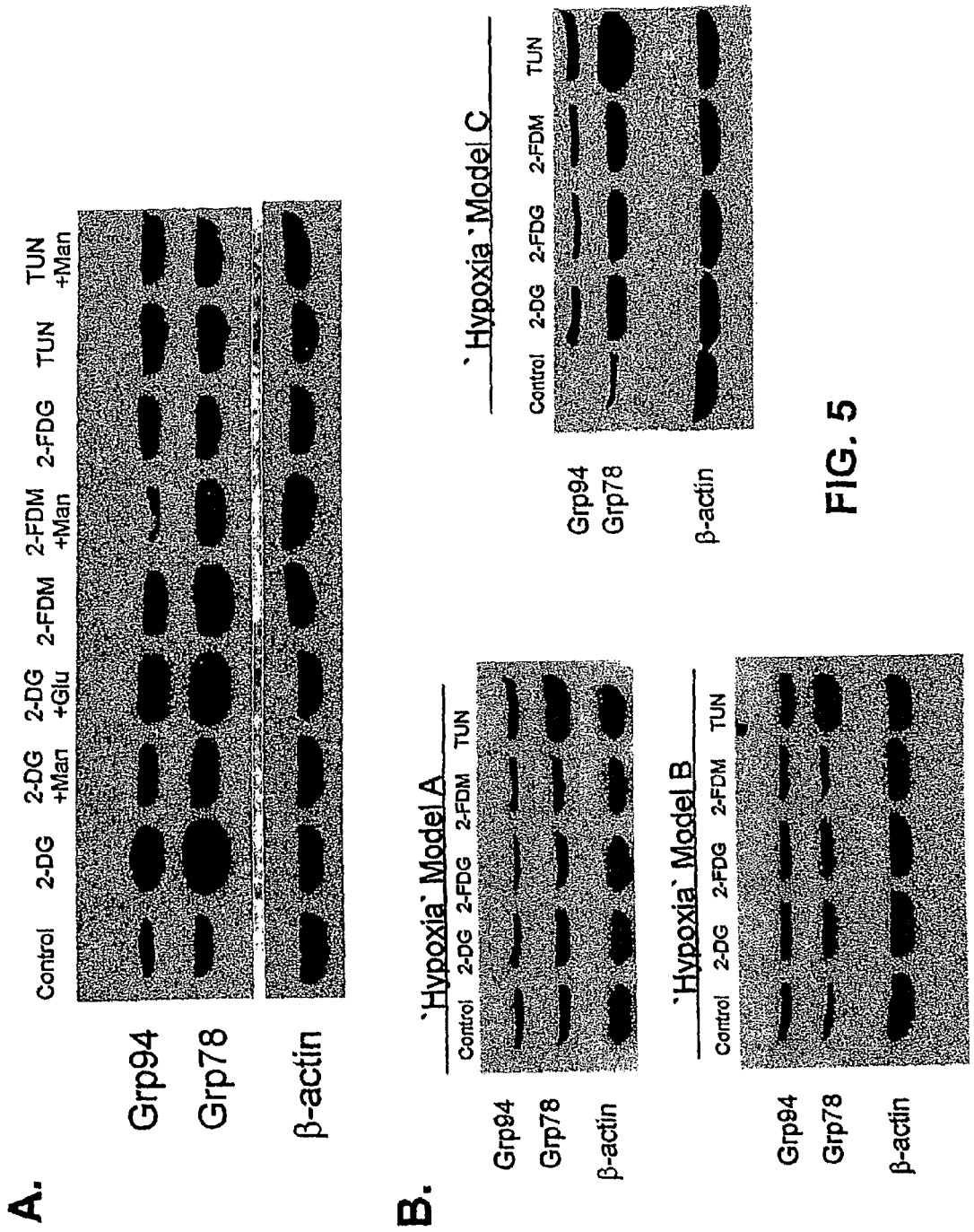
FIG. 5 shows (A) SKBR3 cells were treated with 8 mM of either 2-DG, 2-FDG or 2-FDM for 24 hrs and whole cell lysates were blotted for two molecular chaperones, Grp78 and Grp94. 1 micro g/ml of tunicamycin (TUN) was used as a positive control. Protein loading was verified by β-actin. (B) Western blots of these proteins were assayed when cells in models of "hypoxia" A, B & C were treated with similar doses of these sugar analogs.

Treatment by Either 2-DG or 2-FDM Leads to Unfolded Protein Response in SKBR3 Cells Under Normoxia When the normal process of protein glycosylation is affected, misfolded proteins accumulate in the endoplasmic reticulum (ER) leading to a signaling cascade known as unfolded protein response (UPR). Drugs that interfere with glycosylation have been shown to induce UPR, leading to increases in the protein folding capacity of ER via upregulation of chaperones i.e. Grp78/Bip or Grp94. As shown in FIG. 5A, when SKBR3 cells are treated with 2-DG, 2-FDM, or tunicamycin, a well-known inhibitor of glycosylation, under normoxia, both Grp78 and Grp94 are upregulated. Moreover, addition of 2 mM mannose reverses the 2-DG and 2-FDM upregulation of chaperones but not that of tunicamycin. The mannose reversal of 2-DG induced UPR correlates with data in FIG. 3D demonstrating that the toxicity of 2-DG is reversed by the addition of exogenous mannose; similar results were found in 2-FDM treated cells. As expected, 2-FDG does not increase the levels of these chaperones as much as 2-DG or 2-FDM, correlating with the toxicity data (FIG. 1B) illustrating no cell death in SKBR3 cells when treated under normoxic conditions. In contrast, when 2-DG or 2-FDM are applied to cells growing under three different experimental conditions of hypoxia, no significant upregulation of the UPR is observed in models A and B as compared to model C where both chaperones are upregulated. Moreover, tunicamycin, as a positive control, is shown to induce the synthesis of these chaperones in all three models (FIG. 5B). These results indicate that, when cells are treated with 2-DG or 2-FDM, the mechanism of cell death differs under "hypoxic" (blockage of glycolysis) vs. normoxic (interference with glycosylation) conditions.

Figure 6:
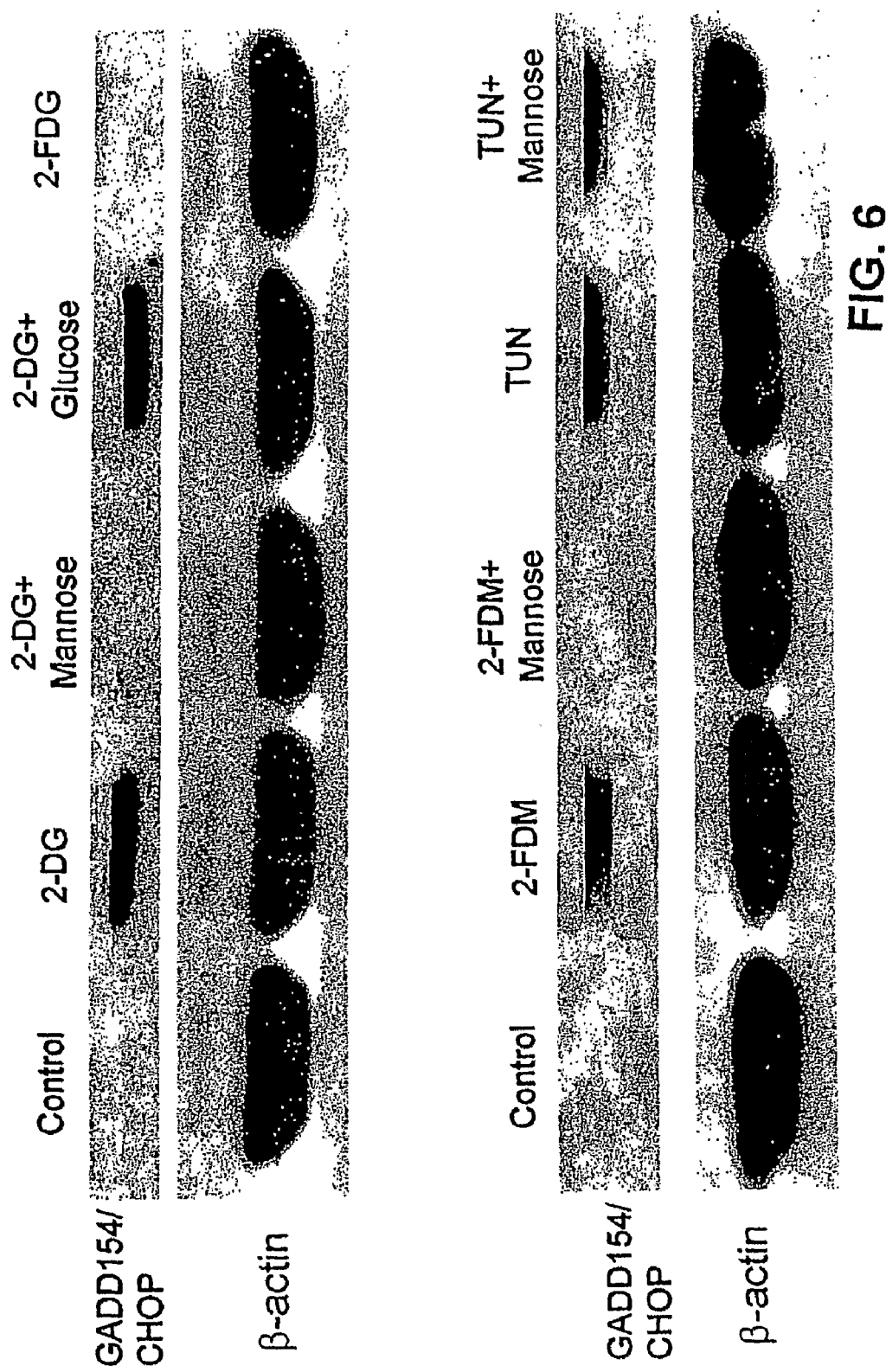
FIG. 6 shows SKBR3 cells were treated with 8 mM of either 2-DG, 2-FDG or 2-FDM for 24 hrs and whole cell lysates were probed for CHOP/GADD154. Induction of CHOP/GADD154 induced by both 2-DG and 2-FDM was reversed by addition of exogenous mannose, whereas glucose showed no effect on the amount of this protein. Tunicamycin was used as a positive control. Protein loading was verified by β-actin.

Toxicity of 2-DG and 2-FDM Correlates with Induction of the UPR-Specific Apoptotic Pathway in SKBR3 Cells It has been reported that when cells cannot overcome ER stress, UPR induces specific apoptotic pathways via induction of GADD154/CHOP (13,14). Thus, to determine whether 2-DG and 2-FDM kill SKBR3 cells due to ER stress under normoxia, this UPR-specific apoptotic protein was assayed using western blot analysis. As can be seen in FIG. 6, following 2-DG, 2-FDM, and tunicamycin, but not 2-FDG treatment, GADD154/CHOP is induced. When this apoptotic pathway is induced by either 2-DG or 2-FDM, it can be reversed by co-treatment with mannose; however, tunicamycin induced GADD154/CHOP cannot be reversed by addition of this sugar. These data correlate with the reversal of cytotoxicity by mannose, as shown in FIG. 2B.

Discussion

Solid tumors contain hypoxic as well as normoxic areas due to insufficient angiogenesis, rapid growth of the tumor and decreased oxygen carrying ability of tumor vessels (15, 16,17). Because the sole energy production pathway in hypoxic cells is glycolysis, it has been shown that the glycolytic inhibitor 2-DG is selectively toxic to these cells but is non-toxic and only growth inhibits aerobic cells (3,6,18,19). However, a select number of tumor cell lines are killed by 2-DG in the presence of oxygen. Among these sensitive cell types is the human breast cancer cell line SKBR3. A deficiency in mitochondrial respiration could explain the sensitivity of these cells to 2-DG, because blockage of glycolysis in cells with compromised mitochondria would lower ATP levels, leading to necrotic cell death (20). However, this possibility was ruled out by oxygen consumption experiments, which showed that SKBR3 cells respire similarly to two other cells lines found to be resistant to 2-DG under normoxia (Table 1). Furthermore, the rate of respiration of cell line 1420, which is also sensitive to 2-DG under normoxia, was found to be higher than in 2-DG resistant cell lines. Thus, the toxicity of 2-DG in SKBR3 under normoxia cannot be explained by a deficiency in mitochondrial function, indicating that the mechanism of cell death is unrelated to the effect of this sugar on blocking glycolysis.

Previously, it was reported that SKBR3 cells were sensitive to 2-DG under normoxia due to inhibition of glycolysis, leading to depletion of ATP pools which resulted in increased expression of glucose transporter-I and greater uptake of 2-DG (10). However, 2-FDG is a more potent inhibitor of glycolysis than 2-DG (11, FIG. 2) but is non-toxic to SKBR3 cells growing under normoxia, further supporting the conclusion that 2-DG kills these cells via a mechanism other than by blockage of glycolysis and inhibition of ATP production.

The data showing that SKBR3 cells are also sensitive to the mannose analog 2-FDM indicates that the manno-configuration of sugar analogs is important for their toxic activity in select tumor cells growing under normoxia. The lack of an oxygen atom at the second carbon of 2-DG renders this compound both a glucose and mannose analog, whereas the fluoro group in 2-FDG renders it a glucose analog only. The conclusion that the manno-configuration is relevant to the toxicity of these sugar analogs is supported by work published in the late 1970s by a group headed by Schwartz.

This group showed that 2-DG, 2-FDG and 2-FDM could interfere with N-linked glycosylation in chick embryo fibroblasts, which were infected with fowl plague virus, resulting in decreased glycoprotein synthesis and viral reproduction (7,8,21-24). Their reports concluded that 2-DG can inhibit the assembly of lipid linked oligosaccharides, which were to be transferred onto the proteins within the endoplasmic reticulum of the cell. It was demonstrated that a metabolite of 2-DG, GDP-2DG, could cause premature termination of the oligosaccharide assembly leading to shortened lipid-linked oligosaccharides not suitable for their transfer onto proteins (8). Overall, these results showed that the potency of these analogs to inhibit viral glycoprotein synthesis was in the order of 2-DG>2-FDM>2-FDG (21), which is similar to the toxicity of these analogs in SKBR3 cells growing under normoxia. This group also reported that the inhibitory effects of these analogs could be reversed by addition of low dose exogenous mannose (7). Similarly, it was found that 1 mM mannose completely reverses 2-DG and 2-FDM toxicity in SKBR3 cells, indicating that both mannose analogs kill these cells via interfering with N-linked glycosylation (7,8,21-24).

Although mannose is a core sugar in N-linked glycosylated proteins, it also can participate in the glycolytic pathway, because it can be converted to fructose-6-phosphate by phosphomannoisomerase. Thus, it remains possible that mannose could reverse the toxicity of 2-DG in SKBR3 cells by circumventing the glycolytic step which 2-DG inhibits (FIG. 7). However, this possibility seems less likely, because 2 mM mannose did not reverse growth inhibition and cell death induced by 2-DG in "hypoxic" models A and B, whereas in model C, in which cells were actually grown under hypoxia, there was a slight recovery effect. This slight recovery could be explained by (1) 2-DG and 2-FDM interfering with glycosylation even under hypoxic conditions, and/or (2) mannose reversing the inhibition of glycolysis in model C, because these cells under 0.5% hypoxia are still undergoing oxidative phosphorylation, albeit reduced. Overall, the reversal of 2-DG and 2-FDM toxicity by mannose in cells sensitive to these sugar analogs under normoxia but not in cells whose mitochondria are shut down (models A and B) supports that interference with glycosylation, and not inhibition of glycolysis, is responsible for the normoxic hypoxia.

When N-linked glycosylation is inhibited, proteins cannot fold properly and are retained in the ER (25,26). Accumulation of unfolded proteins results in distention of the organelle as well as perturbed protein translation. In such an event, cells initiate a complex, but yet conserved, signaling cascade, known as unfolded protein response, (UPR) to reestablish homeostasis in the ER. Three ER transmembrane proteins transduce the unfolded protein signal to the nucleus: inositol requiring enzyme 1 (IRE 1); double-stranded RNA activated protein kinase (PERK), and activating transcription factor 6 (ATF6) (27). When unfolded proteins accumulate in the ER, a molecular chaperone, glucose regulated protein 78 (Grp78/Bip), dissociates from these three ER transmembrane proteins, thereby activating them (28). This results in a number of metabolic and molecular alterations, including upregulation of sugar transporters, increases in phospholipid synthesis, amino acid transport, and expression of molecular chaperones Grp78/Bip and Grp94 (29-31).

2-DG and 2-FDM upregulate the expression of both Grp78 and Grp94 in SKBR3 cells growing under normoxic conditions, which can be reversed by addition of exogenous mannose, strongly supporting that these sugar analogs are interfering with N-linked glycosylation, leading to unfolded proteins and thereby initiating UPR. Furthermore, 2-FDG, which is a better inhibitor of glycolysis than either 2-DG or 2-FDM, is not as effective in inducing a UPR response. The magnitude of the UPR response to these analogs appears to reflect the degree of interference with glycosylation, which agrees with reports demonstrating that 2-DG>2-FDM>2-FDG in blocking lipid linked oligosaccharide assembly in viral coat proteins (21-24). Moreover, this UPR data correlates with the cytotoxicity results, which similarly show that 2-DG>2-FDM>>>2-FDG in growth inhibiting and killing SKBR3 cells under normoxia.

On the other hand, in the "hypoxic" models A and B, Grp78 and Grp94 are not upregulated by 2-DG, indicating that these cells die via inhibition of glycolysis and not through interference with glycosylation. A possible mechanism to explain why UPR is not induced in these models relates to levels of ATP known to be necessary for Grp78/Bip binding unfolded proteins and thereby activating UPR. In contrast to model A and B, UPR is induced in model C (FIG. 5B), where ATP levels are decreased less by 2-DG. Moreover, tunicamycin, which is known not to affect ATP levels significantly, does up-regulate the chaperones in the "hypoxic" models, demonstrating a functional UPR pathway in these cells.

UPR is much like p53, where DNA damage signals cell cycle arrest, activation of DNA repair enzymes, and depending on the outcome of these processes, apoptosis. Thus, if UPR fails to establish homeostasis within the endoplasmic reticulum, ER-stress specific apoptotic pathways are activated (31). Among the mediators of apoptotic pathways which include caspase 4, caspase 12, and CHOP/GADD154, increased activation of the latter has been shown to be a better indicator of the ER-induced mammalian apoptotic pathway (14) than the others. Thus, FIG. 6, where it is shown that expression of CHOP/GADD154 correlates with 2-DG and 2-FDM cytotoxicity in SKBR3 cells growing under normoxia, supports that these sugar analogs are toxic via interference with glycosylation leading to ER stress. Moreover, the reversal of CHOP/GADD154 induction by addition of mannose but not by glucose further supports that 2-DG and 2-FDM are toxic via this mechanism.

A fundamental question is why do certain tumor cell types die when treated with 2-DG in the presence of $O_2$, whereas most tumor as well as normal cells do not. An answer to this question comes from genetic studies in which the enzyme phosphomannoseisomerase is shown to be deleted in patients suffering from what is described as Carbohydrate-Deficient Glycoprotein Syndrome Type 1b (32,33). Deletion of this enzyme results in hypoglycosylation of serum glycoproteins, leading to thrombosis and gastrointestinal disorders characterized by protein-losing enteropathy. When exogenous mannose was added to the diets of these patients, their serum glycoproteins returned to normal, their symptoms disappeared (34,35). This correlates with the instant data showing that exogenous mannose rescues the select tumor cells that are killed when treated with 2-DG in normoxia. It is possible that these types of tumor cells are either down-regulating or defective in phosphomannoseisomerase, or that 2-DG effects this enzyme more in these tumor cells than most others which have shown to be resistant to 2-DG treatment in normoxia. However, as indicated in FIG. 7, there are numerous other steps where 2-DG and 2-FDM may be inhibiting mannose metabolism involved with N-linked glycosylation.

2-DG, 2-CM, and 2-FDM (2-FM) kill certain tumor types via interference with glycosylation leading to ER stress and apoptosis. The finding that 2-FDG does not kill these cells eliminates the possibility that 2-DG and 2-FDM toxicity is due to the inhibition of glycolysis and ATP depletion. These agents can be used as single agent therapies in the treatment of select solid tumors (see FIG. 7).

Example 3

Theranostic Method

A patient cancer tumor sample is obtained by biopsy. The isolated cells are treated with 2-DG, 2-CM, or 2-FM under normoxic conditions and hypoxic conditions to determine if they are sensitive to the mannose analog under normoxic conditions and insensitive to the mannose analog under hypoxic conditions. The detection of sensitivity to the at least one mannose analog under normoxic conditions and lack of sensitivity to the at least one mannose analog under hypoxic conditions results in the determination that the patient cancer tumor sample comprises cells sensitive to killing due to an interference with glycosylation under normoxia. Sensitive cells under normoxic conditions are treated with mannose to confirm that the cytotoxic effects of the 2-DG, 2-CM, or 2-FM treatment are due to an interference with glycosylation.

Alternatively, the molecular signature of cells from a patient cancer tumor sample is compared with the molecular signatures of closely related mannose analog sensitive and resistant cell lines to determine if there is a substantial similarity in the molecular signature of the cells from the patient sample to the molecular signature of a mannose analog sensitive cell line. A substantial similarity in the molecular signature of the cells from the patient sample to the molecular signature of a mannose analog sensitive cell line results in the determination that the patient cancer tumor sample comprises cells sensitive to killing due to an interference with glycosylation under normoxia.

A patient with cancer tumor cells found to be sensitive to glycosylation inhibition is treated with one or more mannose analogs in accordance with the treatment methods of the invention.

While specific embodiments of the invention have been shown and described in detail to illustrate the application of the principles of the invention, it will be understood that the invention may be embodied otherwise without departing from such principles.

LIST OF REFERENCES CITED

1. Brown J M, Wilson W R. Exploiting tumor hypoxia in cancer treatment. Nat Rev Cancer 2004; 4:437-47.
2. Semenza G L. Intratumoral hypoxia, radiation resistance, and HIF-1. Cancer Cell 2004; 5:405-406:
3. Maher J C, Krishan A, Lampidis T J. Greater cell cycle inhibition and cytotoxicity induced by 2-deoxy-D-glucose in tumor cells treated under hypoxic vs aerobic conditions. Cancer Chemother Pharmacol 2004; 53:116-122.
4. Boros L G, Brandes J L, Yusuf F I, Cascante M, Williams R D, Schiermer W J. Inhibition of oxidative and nonoxidative pentose phosphate pathways by somatostatin: a possible mechanism of antitumor action. Med Hypotheses 1998; 50:501.
5. LaManna J C, Lust D. Nutrient consumption and metabolic perturbations. Neurosurg Clin N Am 1997; 8:145-163.
6. Maschek G, Savaraj N, Priebe W, et al. 2-deoxy-D-glucose increases the efficacy of adriamycin and paclitaxel in human osteosarcoma and non-small cell lung cancers in vivo. Cancer Res 2004; 64:31-4.
7. Datema R, Schwarz R T. Interference with glycosylation of glycoproteins. Biochem J 1979; 184: 113-123.
8. Datema R, Schwarz R T. Formation of 2-Deoxyglucose-containing lipid-linked oligosaccharides. Eur J Biochem 1978; 90: 505-516.
9. King M P, Attardi G. Human cells lacking mtDNA: repopulation with exogenous mitochondria by complementation. Science 1989; 246: 500-503.
10. Aft R L, Zhang F W, Gius D. Evaluation of 2-deoxy-D-glucose as a chemotherapeutic agent: mechanism of cell death. Br J Cancer 2002; 87:805-812.
11. Lampidis T J, Kurtoglu M, Maher J C, et al. Efficacy of 2-Halogen Substituted D-Glucose Analogs in Blocking Glycolysis and Killing "Hypoxic Tumor Cells". Cancer Chemother Pharmacol (in press).
12. Protein purification methods: A practical approach. In: Harris E L V, Angal S, editors. New York: IRL Press at Oxford University Press; 1994. p. 270.
13. Xu C, Bailly-Maitre B, Reed J C. Endoplasmic reticulum stress: cell life and death decisions. J Clin Invest 2005; 115:2656-2664.
14. Obeng E A, Boise L H. Caspase-12 and Caspase-4 are not required for caspase-dependent endoplasmic reticulum stress-induced apoptosis. J Biol Chem 2005; 280: 29578-29587.
15. Gillies R J, Raghunand N, Karczmar G S, Bhujwalla Z M. MRI of the tumor microenviroment. J Magn Reson Imaging 2002; 16:430-450.
16. Maxwell P H, Dachs G U, Gleadle J M, et al. Hypoxia-inducible facoro-1 modulates gene expression in solid tumors and influences both angiogenesis and tumor growth. PNAS 1997; 94:8104-8109.
17. Semenza G L. Targeting HIF-1 for cancer therapy. Nature Rev 2003; 3:721-732.
18. Liu H, Hu Y P, Savaraj N, Priebe W, Lampidis T J. Hypersensitization of tumor cells to glycolytic inhibitors. Biochemistry 2001; 40:5542-5547.
19. Liu H, Savaraj N, Priebe W, Lampidis T J. Hypoxia increases tumor cell sensitivity to glycolytic inhibitors: a strategy for solid tumor therapy (Model C). Biochem Pharmacol 2002; 64:1745-1751.
20. Gramaglia D, Gentile A, Battaglia M, et al. Apoptosis to necrosis switching downstream of apoptosome formation requires inhibition of both glycolysis and oxidative phosphorylation in a BCL-$X_L$ and PKB/AKT-independent fashion. Cell Death Differentiation 2004; 11: 342-353.
21. Datema R, Schwarz R T, Jankowski A W. Fluoro-glucose inhibition of protein glycosylation in vivo. Eur J Biochem 1980; 109:331-341.
22. Schmidt M F G, Schwarz R T, Scholtissek C. Nucleoside-diphosphate derivatives of 2-deoxy-D-glucose in animal cells. Eur J Biochem 1974; 49: 237-247.
23. Schmidt M F G, Biely P, Kratky Z, Schwarz R T. Metabolism of 2-deoxy-2-fluoro-D-[$^3$H] glucose and 2-deoxy-2-fluoro-D-[$^3$H] mannose in yeast and chick-embryo cells. Eur J Biochem 1978; 87: 55-68.
24. McDowell W, Datema R, Romero P A, Schwarz R T. Mechanism of inhibition of protein glycosylation by the antiviral sugar analogue 2-deoxy-2-fluoro-d-mannose: Inhibition of synthesis of Man(GlcNAc)$_2$-PP-Dol by the guanosine diphosphate ester. Biochemistry 1985; 24:8145-8152.
25. Ellgaard L, Helenius A. Quality control in the endoplasmic reticulum. Nat Rev Mol Cell Biol 2003; 4:181-191.
26. Parodi A J. Protein glycosylation and its role in protein folding. Annu Rev Biochem 2000; 69: 69-93.
27. Schroder M, Kaufman R J. ER stress and unfolded protein response. Mutat Res 2005; 569:29-63.
28. Pahl H L. Signal transduction from the endoplasmic reticulum to the cell nucleus. Physiol Rev 1999; 79: 683-701.
29. Ma Y, Hendershot L M. The unfolding tale of the unfolded protein response. Cell 2001; 107: 827-830.
30. Doerrler W T, Lehrman M A. Regulation of dolichol pathway in human fibroblasts by the endoplasmic reticulum unfolded protein response. PNAS 1999; 96:13050-13055.
31. Breckenridge D G, Germain M, Mathai J P, Nguyen M, Shore G C. Regulation of apoptosis by endoplasmic reticulum pathways. Oncogene 2003; 22: 8608-8618.
32. Niehues R, Haslik M, Alton G, et al. Carbohydrate-deficient glycoprotein syndrome type Ib. J Clin Invest 1998; 101:1414-1420.
33. Freeze H H. Human disorders in N-glycosylation and animal models. Biochim Biophys Acta 2002; 1573:388-93.
34. Freeze H H. Sweet solution: sugars to the rescue. J Cell Biol 2002; 158:615-616.
35. Paneerselvam K, Freeze H H. Mannose corrects altered N-glycosylation in carbohydrate-deficient glycoprotein syndrome fibroblasts. J Clin Invest 1996; 97:1478-1487.

What is claimed is:

1. A method for treating cancer comprising administering to a patient having a cancer in need of treatment, the cancer having normoxic tumor cells, an effective amount of at least one mannose analog, the mannose analog kills normoxic tumor cells of the cancer due to an interference with glycosylation under aerobic conditions wherein sensitivity to being killed by the at least one mannose analog can be reversed by addition of exogenous mannose.

2. The method of claim 1, including treating the patient with at least one additional anti-tumor treatment.

3. The method of claim 1, wherein the patient is not treated with any additional anti-tumor treatment.

4. The method of claim 1, wherein the mannose analog is 2-DG.

5. The method of claim 1, wherein the normoxic tumor cells of the cancer are human breast cells.

6. The method of claim 5, wherein the sensitivity of the normoxic tumor cells of the cancer to interference with glycosylation under aerobic conditions is similar to that of a cell line selected from the group consisting of SKBR3, 1420, HELA, S-1, S-2, T98G, and RT8228.

7. A method for killing tumor cells in a patient comprising administering to the patient an effective amount of at least one mannose analog, wherein the tumor cells are normoxic and are killed by at least one mannose analog under normoxia and sensitivity to being killed by the at least one mannose analog can be reversed by addition of exogenous mannose.

8. The method of claim 7, including treating the patient with at least one additional anti-tumor treatment.

9. The method of claim 4, wherein the patient is not treated with any additional anti-tumor treatment.

10. The method of claim 4, wherein the mannose analog is 2-DG.

11. The method of claim 7, wherein the normoxic tumor cells are human breast cells.

12. A method of treating glioblastoma in a subject in need thereof comprising the step of administering a therapeutically effective amount of 2-FM, 2-CM or 2-BM to the subject in need thereof, wherein the glioblastoma has normoxic tumor cells, and the therapeutically effective amount of 2-FM, 2-CM, or 2-BM kills normoxic tumor cells of the glioblastoma due to an interference with glycosylation under aerobic conditions, and wherein sensitivity to being killed by the therapeutically effective amount of 2-FM, 2-CM, or 2-BM can be reversed by addition of exogenous mannose.

13. A method of treating pancreatic cancer in a subject in need thereof comprising the step of administering a therapeutically effective amount of 2-FM, 2-CM, or 2-BM to the subject in need thereof, wherein the cancer has normoxic tumor cells, and the therapeutically effective amount of 2-FM, 2-CM, or 2-BM kills normoxic tumor cells of the cancer due to an interference with glycosylation under aerobic conditions, and wherein sensitivity to being killed by the therapeutically effective amount of 2-FM, 2-CM, or 2-BM can be reversed by addition of exogenous mannose.

14. A method of treating the proliferation of tumors in a subject in need thereof comprising the step of administering a therapeutically effective amount of 2-FM, 2-CM, or 2-BM to the subject in need thereof, wherein the tumors have normoxic tumor cells, and the therapeutically effective amount of 2-FM, 2-CM, or 2-BM kills normoxic tumor cells of the tumors due to an interference with glycosylation under aerobic conditions, and wherein sensitivity to being killed by the therapeutically effective amount of 2-FM, 2-CM, or 2-BM can be reversed by addition of exogenous mannose.

15. A method of treatment of cancer in a subject in need thereof comprising the step of administering a therapeutically effective amount of 2-FM, 2-CM, or 2-BM to the subject in need thereof, wherein the cancer has normoxic tumor cells, and the therapeutically effective amount of 2-FM, 2-CM, or 2-BM kills normoxic tumor cells of the cancer due to an interference with glycosylation under aerobic conditions and sensitivity to being killed by the therapeutically effective amount of 2-FM, 2-CM, or 2-BM can be reversed by addition of exogenous mannose, and wherein cancer cell death occurs by autophagy.

16. A method for achieving an effect in a patient having cancer comprising the administration to the patient of a therapeutically effective amount of 2-FM, 2-CM, or 2-BM, wherein the cancer has normoxic tumor cells, and the therapeutically effective amount of 2-FM, 2-CM, or 2-BM kills normoxic tumor cells of the cancer due to an interference with glycosylation under aerobic conditions and sensitivity to being killed by the therapeutically effective amount of 2-FM, 2-CM, or 2-BM can be reversed by addition of exogenous mannose, and wherein the effect is selected from cell death of pancreatic cancer cells and cell death of glioblastoma cells.

17. A method of treating high grade, highly glycolic gliomas in a subject in need thereof comprising the step of administering a therapeutically effective amount of 2-DG to the gliomas in the subject in need thereof, wherein the gliomas have normoxic tumor cells, and the therapeutically effective amount of 2-DG kills normoxic tumor cells of the gliomas due to an interference with glycosylation under aerobic conditions such that cell death of the gliomas occurs and wherein sensitivity to being killed by the therapeutically effective amount of 2-DG can be reversed by addition of exogenous mannose.

* * * * *